(12) United States Patent
Rowe et al.

(10) Patent No.: US 6,816,605 B2
(45) Date of Patent: *Nov. 9, 2004

(54) METHODS AND SYSTEMS FOR BIOMETRIC IDENTIFICATION OF INDIVIDUALS USING LINEAR OPTICAL SPECTROSCOPY

(75) Inventors: Robert K. Rowe, Corrales, NM (US); Stephen P. Corcoran, Corrales, NM (US); Kristin A. Nixon, Albuquerque, NM (US)

(73) Assignee: Lumidigm, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/407,589

(22) Filed: Apr. 3, 2003

(65) Prior Publication Data

US 2003/0223621 A1 Dec. 4, 2003

Related U.S. Application Data

(63) Continuation-in-part of application No. 09/832,534, filed on Apr. 11, 2001, now Pat. No. 6,560,352, which is a continuation-in-part of application No. 09/415,594, filed on Oct. 8, 1999, now Pat. No. 6,628,809.

(51) Int. Cl.[7] .............................................. G06K 9/00
(52) U.S. Cl. .................... 382/115; 356/71; 250/5.52; 250/5.82; 250/339.02
(58) Field of Search ............................... 382/115, 116, 382/124–127; 356/71; 340/5.52, 5.82; 250/339.02

(56) References Cited

U.S. PATENT DOCUMENTS

| | | |
|---|---|---|
| 3,508,830 A | 4/1970 | Hopkins et al. |
| 3,872,443 A | 3/1975 | Ott .............................. 600/587 |
| 3,910,701 A | 10/1975 | Henderson et al. |
| RE29,008 E | 10/1976 | Ott ........................... 340/172.5 |
| 4,035,083 A | 7/1977 | Woodriff et al. |
| 4,142,797 A | 3/1979 | Astheimer |
| 4,169,676 A | 10/1979 | Kaiser |
| 4,260,220 A | 4/1981 | Whitehead |
| 4,427,889 A | 1/1984 | Muller |
| 4,537,484 A | 8/1985 | Fowler et al. |

(List continued on next page.)

FOREIGN PATENT DOCUMENTS

| | | |
|---|---|---|
| EP | 0 280 418 A1 | 8/1988 |
| EP | 0 426 358 B1 | 5/1991 |
| EP | 0 449 335 A2 | 10/1991 |

(List continued on next page.)

OTHER PUBLICATIONS

Anderson, C. E. et al., "Fundamentals of Calibration Transfer Procrustes Analysis," Appln. Spectros., vol. 53, No. 10 (1999) p. 1268–1276.

(List continued on next page.)

*Primary Examiner*—Brian Werner
(74) *Attorney, Agent, or Firm*—Townsend and Townsend and Crew LLP

(57) ABSTRACT

Methods and systems are provided for identifying an individual. Electromagnetic radiation is propagated into tissue of the individual. A measured spectral variation is received in the form of electromagnetic radiation scattered from the tissue of the individual. The measured spectral variation is compared with a previously stored spectral variation over a predetermined wavelength interval. The comparison is performed at each of multiple wavelengths within the predetermined wavelength interval and is performed of a property of the measured and previously stored spectral variations that is independent of a presence of other wavelengths. The individual is designated as having an identity associated with the previously stored spectral variation if the measured spectral variation is consistent with the previously stored spectral variation.

40 Claims, 7 Drawing Sheets

U.S. PATENT DOCUMENTS

| | | |
|---|---|---|
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |
| 4,657,397 A | 4/1987 | Oehler et al. |
| 4,661,706 A | 4/1987 | Messerschmidt et al. |
| 4,684,255 A | 8/1987 | Ford |
| 4,712,912 A | 12/1987 | Messerschmidt |
| 4,730,882 A | 3/1988 | Messerschmidt |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,944,021 A | 7/1990 | Hoshino et al. |
| 4,975,581 A | 12/1990 | Robinson et al. ............ 250/339 |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,068,536 A | 11/1991 | Rosenthal |
| 5,070,874 A | 12/1991 | Barnes et al. |
| 5,158,082 A | 10/1992 | Jones |
| 5,163,094 A | 11/1992 | Prokoski et al. |
| 5,178,142 A | 1/1993 | Harjunmaa et al. |
| 5,179,951 A | 1/1993 | Knudson |
| 5,204,532 A | 4/1993 | Rosenthal |
| 5,222,495 A | 6/1993 | Clarke et al. |
| 5,222,496 A | 6/1993 | Clarke et al. |
| 5,223,715 A | 6/1993 | Taylor |
| 5,225,678 A | 7/1993 | Messerschmidt |
| 5,230,702 A | 7/1993 | Lindsay et al. |
| 5,237,178 A | 8/1993 | Rosenthal et al. |
| 5,243,546 A | 9/1993 | Maggard |
| 5,257,086 A | 10/1993 | Fateley et al. |
| 5,267,152 A | 11/1993 | Yang et al. |
| 5,268,749 A | 12/1993 | Weber et al. |
| 5,291,560 A | 3/1994 | Daugman |
| 5,299,570 A | 4/1994 | Hatschek |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,348,003 A | 9/1994 | Caro |
| 5,351,686 A | 10/1994 | Steuer et al. |
| 5,355,880 A | 10/1994 | Thomas et al. |
| 5,360,004 A | 11/1994 | Purdy et al. |
| 5,361,758 A | 11/1994 | Hall et al. |
| 5,366,903 A | 11/1994 | Lundsgaard et al. |
| 5,372,135 A | 12/1994 | Mendelson et al. |
| 5,379,764 A | 1/1995 | Barnes et al. |
| 5,402,778 A | 4/1995 | Chance |
| 5,405,315 A | 4/1995 | Khuri et al. |
| 5,419,321 A | 5/1995 | Evans |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,494,032 A | 2/1996 | Robinson et al. |
| 5,505,726 A | 4/1996 | Meserol |
| 5,507,723 A | 4/1996 | Keshaviah |
| 5,515,847 A | 5/1996 | Braig et al. |
| 5,518,623 A | 5/1996 | Keshaviah et al. |
| 5,523,054 A | 6/1996 | Switalski et al. |
| 5,533,509 A | 7/1996 | Koashi |
| 5,537,208 A | 7/1996 | Bertram et al. |
| 5,539,207 A | 7/1996 | Wong et al. |
| 5,552,997 A | 9/1996 | Massart |
| 5,559,504 A | 9/1996 | Itsumi et al. |
| 5,596,992 A | 1/1997 | Haaland et al. |
| 5,606,164 A | 2/1997 | Price et al. |
| 5,630,413 A | 5/1997 | Thomas et al. |
| 5,636,633 A | 6/1997 | Messerschmidt et al. |
| 5,655,530 A | 8/1997 | Messerschmidt ............ 128/633 |
| 5,672,864 A | 9/1997 | Kaplan |
| 5,672,875 A | 9/1997 | Block et al. |
| 5,677,762 A | 10/1997 | Ortyn et al. |
| 5,681,273 A | 10/1997 | Brown |
| 5,708,593 A | 1/1998 | Saby et al. |
| 5,719,950 A | 2/1998 | Osten et al. |
| 5,724,268 A | 3/1998 | Sodickson et al. |
| 5,737,439 A | 4/1998 | Lapsley et al. |
| 5,743,262 A | 4/1998 | Lepper, Jr. et al. |
| 5,747,806 A | 5/1998 | Khalil et al. |
| 5,750,994 A | 5/1998 | Schlager |
| 5,751,835 A | 5/1998 | Topping et al. |
| 5,761,330 A | 6/1998 | Stoianov et al. |
| 5,782,755 A | 7/1998 | Chance et al. |
| 5,792,050 A | 8/1998 | Alam et al. |
| 5,792,053 A | 8/1998 | Skladner et al. |
| 5,793,881 A | 8/1998 | Stiver et al. |
| 5,808,739 A | 9/1998 | Turner et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,850,623 A | 12/1998 | Carman, Jr. et al. |
| 5,853,370 A | 12/1998 | Chance et al. |
| 5,857,462 A | 1/1999 | Thomas et al. |
| 5,860,421 A | 1/1999 | Eppstein et al. |
| 5,867,265 A | 2/1999 | Thomas |
| 5,886,347 A | 3/1999 | Inoue et al. |
| 5,902,033 A | 5/1999 | Levis et al. |
| 5,914,780 A | 6/1999 | Turner et al. |
| 5,933,792 A | 8/1999 | Anderson et al. |
| 5,935,062 A | 8/1999 | Messerschmidt et al. |
| 5,945,676 A | 8/1999 | Khalil |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |
| 5,987,346 A | 11/1999 | Benaron et al. |
| 5,999,637 A | 12/1999 | Toyoda et al. |
| 6,005,722 A | 12/1999 | Butterworth et al. |
| 6,016,435 A | 1/2000 | Maruo et al. |
| 6,025,597 A | 2/2000 | Sterling et al. |
| 6,026,314 A | 2/2000 | Amerov et al. |
| 6,028,773 A | 2/2000 | Hundt ....................... 361/760 |
| 6,031,609 A | 2/2000 | Funk et al. |
| 6,034,370 A | 3/2000 | Messerschmidt |
| 6,040,578 A | 3/2000 | Malin et al. |
| 6,041,247 A | 3/2000 | Weckstrom et al. |
| 6,041,410 A | 3/2000 | Hsu et al. |
| 6,043,492 A | 3/2000 | Lee et al. |
| 6,044,285 A | 3/2000 | Chaiken et al. |
| 6,045,502 A | 4/2000 | Eppstein et al. |
| 6,046,808 A | 4/2000 | Fately |
| 6,049,727 A | 4/2000 | Crothall |
| 6,056,738 A | 5/2000 | Marchitto et al. |
| 6,057,925 A | 5/2000 | Anthon |

| | | | |
|---|---|---|---|
| 6,061,581 A | 5/2000 | Alam et al. | |
| 6,061,582 A | 5/2000 | Small et al. | |
| 6,066,847 A | 5/2000 | Rosenthal | |
| 6,069,689 A | 5/2000 | Zeng et al. | |
| 6,070,093 A | 5/2000 | Oosta et al. | |
| 6,073,037 A | 6/2000 | Alam et al. | |
| 6,088,605 A | 7/2000 | Griffith et al. | |
| 6,088,607 A | 7/2000 | Diab et al. | |
| 6,100,811 A | 8/2000 | Hsu et al. | |
| 6,115,484 A | 9/2000 | Bowker et al. | |
| 6,115,673 A | 9/2000 | Malin et al. | |
| 6,122,042 A | 9/2000 | Wunderman et al. | 356/73 |
| 6,122,394 A | 9/2000 | Neukermans et al. | |
| 6,141,101 A | 10/2000 | Bleier et al. | |
| 6,147,749 A | 11/2000 | Kubo et al. | |
| 6,148,094 A | 11/2000 | Kinsella | |
| 6,152,876 A | 11/2000 | Robinson et al. | |
| 6,154,658 A | 11/2000 | Caci | |
| 6,157,041 A | 12/2000 | Thomas et al. | |
| 6,159,147 A | 12/2000 | Lichter et al. | |
| 6,172,743 B1 | 1/2001 | Kley et al. | |
| 6,175,407 B1 | 1/2001 | Sartor | |
| 6,181,414 B1 | 1/2001 | Raz et al. | |
| 6,181,958 B1 | 1/2001 | Steuer et al. | |
| 6,212,424 B1 | 4/2001 | Robinson | |
| 6,226,541 B1 | 5/2001 | Eppstein et al. | |
| 6,230,034 B1 | 5/2001 | Messerschmidt et al. | |
| 6,240,306 B1 | 5/2001 | Rohrscheib et al. | |
| 6,240,309 B1 | 5/2001 | Yamashita et al. | |
| 6,241,663 B1 | 6/2001 | Wu et al. | |
| 6,256,523 B1 | 7/2001 | Diab et al. | |
| 6,272,367 B1 | 8/2001 | Chance | |
| 6,280,381 B1 | 8/2001 | Malin et al. | |
| 6,285,895 B1 | 9/2001 | Ristolainen et al. | |
| 6,301,815 B1 | 10/2001 | Sliwa | |
| 6,304,767 B1 | 10/2001 | Soller et al. | |
| 6,307,633 B1 | 10/2001 | Mandella et al. | |
| 6,309,884 B1 | 10/2001 | Cooper et al. | |
| 6,317,507 B1 | 11/2001 | Dolfing et al. | |
| 6,330,346 B1 | 12/2001 | Peterson et al. | 382/115 |
| 6,504,614 B1 | 1/2003 | Messerschmidt et al. | 356/455 |
| 6,560,352 B2 | 5/2003 | Rowe et al. | 382/115 |
| 6,574,490 B2 | 6/2003 | Abbink et al. | 600/316 |
| 2002/0171834 A1 | 11/2002 | Rowe et al. | 356/418 |
| 2002/0183624 A1 | 12/2002 | Rowe et al. | |

FOREIGN PATENT DOCUMENTS

| | | |
|---|---|---|
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |
| EP | 0 801 297 A1 | 10/1997 |
| EP | 0 836 083 A1 | 4/1998 |
| EP | 0 843 986 A2 | 5/1998 |
| EP | 0 869 348 A2 | 10/1998 |
| EP | 0 897 164 A2 | 2/1999 |
| EP | 0 897 691 A2 | 2/1999 |
| EP | 0 317 121 B1 | 5/1999 |
| EP | 0 924 656 A2 | 6/1999 |
| EP | 0 982 583 A1 | 3/2000 |
| EP | 0 990 945 A1 | 4/2000 |
| WO | WO 92/00513 A1 | 1/1992 |
| WO | WO 92/17765 A1 | 10/1992 |
| WO | WO 93/00855 A1 | 1/1993 |
| WO | WO 93/07801 A1 | 4/1993 |
| WO | WO 95/22046 A1 | 8/1995 |
| WO | WO 97/23159 A1 | 7/1997 |
| WO | WO 97/27800 A1 | 8/1997 |
| WO | WO 97/28437 A1 | 8/1997 |
| WO | WO 97/28438 A1 | 8/1997 |
| WO | WO 98/01071 A1 | 1/1998 |
| WO | WO 98/37805 A1 | 9/1998 |
| WO | WO 98/40723 A1 | 9/1998 |
| WO | WO 99/09395 A1 | 2/1999 |
| WO | WO 01/15596 A1 | 3/1999 |
| WO | WO 99/37203 A2 | 7/1999 |
| WO | WO 99/43255 A1 | 9/1999 |
| WO | WO 99/46731 A1 | 9/1999 |
| WO | WO 99/55222 A1 | 11/1999 |
| WO | WO 99/56616 A1 | 11/1999 |
| WO | WO 01/18332 A1 | 3/2001 |
| WO | WO 01/27882 A2 | 4/2001 |
| WO | WO 01/52180 A1 | 7/2001 | G06K/9/00 |
| WO | WO 01/52726 A1 | 7/2001 | A61B/5/00 |
| WO | WO 01/53805 A1 | 7/2001 | G01N/21/35 |
| WO | WO 02/084605 A2 | 10/2002 |
| WO | WO 02/099393 A2 | 12/2002 |

OTHER PUBLICATIONS

Ashbourn, Julian, Biometrics; Advanced Identity Verification, Springer, 2000, pp. 63–64).

Bantle, John P. et al., "Glucose Measurement in Patients with Diabetes Mellitus with Dermal Interstitial Fluid," Copyright © 1997 by Mosby–Year Book, Inc., 9 pages.

Berkoben et al., "Vascular Access for Hemodialysis", *Clinical Dialysis*, published on or before Oct. 30, 1997, 20 pages.

Blank, T.B. et al., "Transfer of Near–Infrared Multivariate Calibrations Without Standards," Anal. Chem., vol. 68 (1996) p. 2987.

Bleyer et al., "The costs of Hospitalizations Due to Hemodialysis Access Management", *Nephrology News & Issues*, Jan., 1995, pp. 19, 20 and 22..

Brasunas John C. et al., "Uniform Time–Sampling Fourier Transform Spectroscopy," Applied Optics, vol. 36, No. 10, Apr. 1, 1997, pp. 2206–22 10.

Brault, James W., "New Approach to High–Precision Fourier Transform Spectrometer Design," Applied Optics, Vo. 35, No. 16, Jun. 1, 1996, pp. 2891–2896.

Cassarly, W.J. et al., "Distributed Lighting Systems: Uniform Light Delivery," Source Unknown, pp. 1698–1702.

Chang, Chong–Min et al., "An Uniform Rectangular Illuminating Optical System for Liquid Crystal Light Valve Projectors," Euro Display '96 (1996) pp. 257–260.

Coyne, Lawrence J. et al., "Distributive Fiber Optic couplers Using Rectangular Lightguides as Mixing Elements," (Information Gatekeepers, Inc. Brookline, MA, 1979) pp. 160–164.

Daugirdas et al., "Comparison of Methods to Predict the Equilibrated Kt/V (eKt/V) in the Hemo Study", National Institutes of Health, NIDDK, Bethesda, MD, Aug. 20, 1996.

de Noord, Onno E., "Multivariate Calibration Standardization," Chemometrics and intelligent Laboratory Systems 25, (1994) pp. 85–97.

Depner et al., "Clinical Measurement of Blood Flow in Hemodialysis Access Fistulae and Grafts by Ultrasound Dilution", from the Department of Nephrology, University of California, published bon or before Oct. 30, 1997, 4 pages.

Despain, Alvin M. et al., "A Large–Aperture Field–Widened Interferometer–Spectrometer for Airglow Studies," Aspen International Conference on Fourier Spectroscopy, 1970, pp. 293–300.

Faber, Nicolaas, "Multivariate Sensitivity for the Interpretation of the Effect of Spectral Pretreatment Methods on Near–Infrared Calibration Model Predictions," Analytical Chemistry, vol. 71, No. 3, Feb. 1, 1999, pp. 557–565.

Geladi, Paul et al., "A Multivariate NIR Study of Skin Alterations in Diabetic Patients as Compared to Control Subjects" J. Near Infrared Sepctrosc., vol. 8 (2000) pp. 217–227.

Haaland, David M. et al. "Reagentless Near–Infrared Determination of Glucose in Whole Blood Using Multivariate Calibration," Applied Spectroscopy, vol. 46, No. 10 (1992) pp. 1575–1578.

Hakim et al., "Effects of Dose of Dialysis on Morbidity and Mortality", American Journal of Kidney Diseases, vol. 23, No. 5, May 1994, pp. 661–669.

Harwit, M. et al., "Chapter 5—Instrument Considerations" Hadamard Transform Optics, Academic Press (1979) pp. 109–145.

Heise H. Michael et al., "Near–Infrared Reflectance Spectroscopy for Noninvasive Monitoring of Metabolites," Clin. Chem. Lab. Med. 2000, 38(2) (2000) pp. 137–145.

Heise, H.M. et al., "Near Infrared Spectrometric Investigation of Pulsatile Blood Flow for Non Invasive Metabolite Monitoring," CP430, Fourier Transform Spectroscopy: 11th International Conference, (1998) pp. 282–285.

Heise, H.M. et al., "Noninvasive Blood Glucose Sensors Based on Near–Infrared Spectroscopy," Artif Organs, vol. 18, No. 6 (1994) pp. 1–9.

Heise, H.M. "Non–Invasive Monitoring of Metabolites Using Near Infrared Spectroscopy: State of the Art," Horm. Metab. Res., vol. 28 (1996) pp. 527–534.

Hopkins, George W. et al., "In–vivo NIR Diffuse–reflectance Tissue Spectroscopy of Human Subjects," SP1E, vol. 3597, Jan. 1999, pp. 632–641.

Jacobs, et al., "A Disposable Urea Sensor for Continuous Monitoring of Hemodialysis Efficiency", USAIO Journal. 1993, pp. M353–M358.

Jagemann, Kay–Uwe et al. "Application of Near–Infrared Spectroscopy for Non–Invasive Determination of Blood/Tissue Glucose Using Neural Networks," Zeitschrift for Physikalische Chemie, Bd.191, S. 179–190 (1995).

Keshaviah et al., "On–line monitoring of the delivery of the hemodialysis prescription", Pediatric Nephrology, vol. 9, 1995, pp. S2–S8.

Khalil, Omar S., "Spectroscopic and Clinical Aspects of Noninvasive Glucose Measurements," Clinical Chemistry, 45:2 (1999) pp. 165–177.

Kohl, Matthias et al., "The Influence of Glucose Concentration Upon the Transport of Light in Tissue–simulating Phantoms," Phys. Med. Biol., vol. 40 (1995) pp. 1267–1287.

Korte, E.H. et al., "Infrared Diffuse Reflectance Accessory for Local Analysis on Bulky Samples," Applied Spectroscopy, vol. 42, No. 1, Jan. 1988, pp. 38–43.

Krivitski, "Theory and Validation of Access Flow Measurement by Dilution Technique During Hemodialysis", Kidney International, vol. 48, 1995, pp. 244–250.

Kumar, G. et al., "Optimal Probe Geometry for Near–Infrared Spectroscopy of Biological Tissue," Applied Spectroscopy, vol. 36 (1997) p. 2286.

Lorber, Avraham et al., "Local Centering in Multivariate Calibration," Journal of Chemometrics, vol. 10 (1996) pp. 215–220.

Lorber, Avraham et al., "Net Analyte Signal Calculation in Multivariate Calibration," Analytical Chemistry, vol. 69, No. 8, Apr. 15, 1997, pp. 1620–1626.

Marbach, Ralf, "Measurement Techniques for IR Spectroscopic Blood Glucose Determination," (1994) pp. 1–158.

Marbach, R. et al. "Noninvasive Blood Glucose Assay by Near–Infrared Diffuse Reflectance Spectroscopy of the Human Inner Lip," Applied Spectroscopy, vol. 47, No. 7 (1993) pp. 875–881.

Marbach, R. et al. "Optical Diffuse Reflectance Accessory for Measurements of Skin Tissue by Near–Infrared Spectroscopy," Applied Optics, vol. 34, No. 4, Feb. 1, 1995, pp. 610–621.

Mardia, K.V. et al., Multivariate Analysis, Academic Press (1979) pp. 300–325.

Martens, Harald et al., Updating Multivariate Calibrations of Process NIR Instruments, Adv. Instru. Control (1990) pp. 371–381.

McIntosh, Bruce C. et al. "Quantitative Reflectance Spectroscopy in the Mid–IR", 16' Annual FACSS Conference, Oct. 1989.

Nichols, et al., "Design and Testing of A White–Light, Steady–State Diffuse Reflectance Spectrometer for Determination of Optical Properties of Highly Scattering Systems," Applied Optics, Jan. 1, 1997, 36(1), pp 93–104.

Offner, A., "New Concepts in Projection Mask Aligners," Optical Engineering, vol. 14, No. 2, Mar.–Apr. 1975 pp. 130–132.

Osborne, B.G. et al., "Optical Matching of Near Infrared Reflectance Monochromator Instruments for the Analysis of Ground and Whole Wheat," J. Near Infared Spectrosc., vol. 7 (1999) p. 167.

Ozdemir, d. et al., "Hybrid Calibration Models: An Alternative to Calibration Transfer," Applied Spectros., vol. 52, No. 4, 1998, p. 599–603.

Powell, J.R. et al., "An Algorithm for the Reproducible Spectral Subtraction of Water from the FT IR Spectra of Proteins in Dilute Solutions and Adsorbed Monolayers," Applied Spectroscopy, vol. 40, No. 3 (1986) pp.339–344.

Ripley, B.D., Pattern Recognition and Neural Networks, Cambridge University Press (1996) pp. 91–120.

Robinson, M. Ries et al., "Noninvasive Glucose Monitoring in Diabetic Patients: A Preliminary Evaluation," Clinical Chemistry, vol. 38, No. 9 (1992) pp. 1618–1622.

Ronco et al., "On–line urea monitoring: a further step towards adequate dialysis prescription and delivery", Int'l. Journal of Artificial Organs, vol. 18, No. 9, 1995, pp. 534–543.

Royston, David D. et al., "Optical Properties of Scattering and Absorbing Materials Used in the Development of Optical Phantoms at 1064 NM," Journal of Biomedical Optics, vol. 1, No. 1, Jan. 1996, pp. 110–116.

Rutan, Sarah C. et al., "Correction for Drift in Multivariate Systems Using the Kalman Filter," Chemometrics and Intelligent Laboratory Systems 35, (1996) pp. 199–211.

Salit, M.L. et al., "Heuristic and Statistical Algorithms for Automated Emission Spectral Background Intensity Estimation," Applied Spectroscopy, vol. 48, No. 8 (1994) pp. 915–925.

Saptari, Vidi Alfandi, "Analysis, Design and Use of a Fourier–Transform Spectrometer for Near Infrared Glucose Absorption Measurement," (Massachusetts Institute of Technology, 1999) pp. 1–76.

Schmitt, J.M. et al., "Spectral Distortions in Near–Infrared Spectroscopy of Turbid Materials," Applied Spectroscopy, No. 50 (1996) p. 1066.

Service, F. John et al., "Dermal Interstitial Glucose as an Indicator of Ambient Glycemia," Diabetes Care, vol. 20, No. 9, Sep. 1997, 9 pages.

Shroder, Robert, Slides from MicroPac Forum Presentation, Current performance results, May 11, 2000; slides 2,4,14.

Sherman, "Recirculation in the Hemodialysis Access", *Principles and Practice of Dialysis*, 1994, pp. 38–46.

Sherman, "The Measurement of Dialysis Access Recirculation", *American Journal of Kidney Diseases*, vol. 22, No. 4, Oct. 1993, pp. 616–621.

Sjoblom, J. et al., "An Evaluation of Orthogonal Signal correction Applied to Calibration Transfer of Near Infrared Spectra," Chemom & Intell Lab. Systems, vol. 44 (1998) p. 229–244.

Steel, W.H., "Interferometers for Fourier Spectroscopy," Aspen International Conference on Fourier Spectroscopy, (1970) pp. 43–53.

Sternberg R.S. et al., "A New Type of Michelson Interference Spectrometer," Sci. Instrum., vol. 41 (1964) pp. 225–226.

Steuer et al., "A New Optical Technique for Monitoring Hematocrit and Circulating Blood Volume: Its Application in Renal Dialysis", *Dialysis & Transplantation*, vol. 22, No. 5, May 1993, pp. 260–265.

Stork, Chris L. et al., "Weighting Schemes for Updating Regression Models—a Theoretical Approach," Chemometrics and Intelligent Laboratory Systems 48, (1999) pp. 151–166.

Sum, Stephen T. et al., "Standardization of Fiber–Optic Probes for Near–Infrared Multivariate Calibrations," Applied Spectroscopy, vol. 52, No. 6 (1998) pp. 869–877.

Swierenga, H. et al., "Comparison of Two Different Approaches Toward Model Transferability in NIR Spectroscopy," Applied Spectroscopy, vol. 52, No. 1 (1998) pp. 7–16.

Swierenga, H. et al., "Improvement of PLS Model Transferability by Robust Wavelength Selection," Chemometrics and Intelligent Laboratory Systems, vol. 41 (1998) pp. 237–248.

Swierenga, H. et al., "Strategy for Constructing Robust Multivariate Calibration Models," Chemometrics and Intelligent Laboratory Systems, vol. 49, (1999) pp. 1–17.

Teijido, J.M. et al., "Design of a Non–conventional Illumination System Using a Scattering Light Pipe," SPIE, Vo. 2774 (1996) pp. 747–756.

Teijido, J.M. et al., "Illumination Light Pipe Using Micro–Optics as Diffuser," SPIE, vol. 2951 (1996) pp. 146–155.

Thomas, Edward V. et al., "Development of Robust Multivariate Calibration Models," Technometrics, vol. 42, No. 2, May 2000, pp. 168–177.

Tipler, Paul A., *Physics*, Second Edition, Worth Publishers, Inc., Chapter 34, Section 34–2, Nov. 1983, pp. 901–908.

Wang, Y–D. et al., "Calibration Transfer and Measurement Stability of Near–Infrared Spectrometers," Appl. Spectros., vol. 46, No. 5 (1992) pp. 764–771.

Wang, Y–D. et al., "Improvement of Multivariate Calibration Through Instrument Standardization," Anal. Chem., vol. 64 (1992) pp. 562–564.

Wang, Z., "Additive Background Correction in Multivariate Instrument Standardization," Anal. Chem., vol. 67 (1995) pp. 2379–2385.

Ward, Kenneth J. et al., "Post–Prandial Blood Glucose Determination by Quantitative Mid–Infrared Spectroscopy," Applied Spectroscopy_, vol. 46, No. 6 (1992) pp. 959–965.

Webb, Paul, "Temperatures of Skin, Subcutaneous Tissue, Muscle and Core in Resting Men in Cold, Comfortable and Hot Conditions," *European Journal of Applied Physiology*, vol. 64 (1992) pp. 471–476.

Whitehead, L.A. et al., "High–efficiency Prism Light Guides with Confocal Parabolic Cross Sections," Applied Optics, vol. 37, No. 22 (1998) pp. 5227–5233.

Brochure entitled "Determination of Delivered Therapy Through Measurement of Effective Clearance", Feresenius USA, Dec. 1994, 1 page.

METHODS AND SYSTEMS FOR BIOMETRIC IDENTIFICATION OF INDIVIDUALS USING LINEAR OPTICAL SPECTROSCOPY

CROSS REFERENCE TO RELATED APPLICATIONS

This application is a continuation-in-part of U.S. patent application Ser. No. 09/832,534, U.S. Pat. No. 6,560,352 entitled "APPARATUS AND METHOD OF BIOMETRIC IDENTIFICATION OR VERIFICATION OF INDIVIDUALS USING OPTICAL SPECTROSCOPY," filed Apr. 11, 2001 by Robert K. Rowe et al., which is a continuation-in-part of U.S. patent application Ser. No. 09/415,594, U.S. Pat. No. 6,628,809, entitled "APPARATUS AND METHOD FOR IDENTIFICATION OF INDIVIDUALS BY NEAR-INFRARED SPECTRUM," filed Oct. 8, 1999 by Robert K. Rowe et al., the entire disclosures of both of which are incorporated herein by reference.

This application is also related to U.S. Pat. Nos. 5,935,062 and 6,152,876, the entire disclosures of both of which are incorporated herein by reference.

BACKGROUND OF THE INVENTION

This application relates generally to methods and systems for performing biometric identifications. More specifically, this application relates to methods and systems for performing biometric identification of individuals using linear optical spectroscopy.

Biometric identification describes the process of using one or more physical or behavioral features to identify a person or other biological entity. There are two common modes in which biometric identification occurs: one-to-many (identification) and one-to-one (verification). One-to-many identification attempts to answer the question of, "do I know you?" The biometric measurement device collects a set of biometric data from a target individual. From this information alone it assesses whether the person was previously enrolled in the biometric system. Systems that perform the one-to-many identification task such as the FBI's Automatic Fingerprint Identification System (AFIS) are generally very expensive (several million dollars or more) and require many minutes to detect a match between an unknown sample and a large database containing hundreds of thousands or millions of entries. The one-to-one mode of biometrics answers the question of, "are you who you say you are?" This mode is used in cases where an individual makes a claim of identity using a code, magnetic card, or other means, and the device uses the biometric data to confirm the identity of the person by comparing the target biometric data with the enrolled data that corresponds with the purported identity.

There also exists at least one variant between these two modes. This variant occurs in the case where a small number of individuals are contained in the enrolled database and the biometric application requires the determination of only whether a target individual is among the enrolled set. In this case, the exact identity of the individual is not required and thus the task is somewhat different (and often easier) than the identification task described above. This variant might be useful in applications where the biometric system is used to secure an expensive, dangerous, or complex piece of machinery. In this example, only authorized people should be able to use the equipment, but it might not be of interest to determine specifically which of the authorized personnel are using it at a particular time.

Although in general the one-to-many identification task is more difficult than one-to-one, the two tasks become the same as the number of recognized or authorized users for a given biometric device decreases to just a single individual. Situations in which a biometric identification task has only a small number of entries in the authorization database are quite common. For example, biometric access to a residence, to a personal automobile, to a personal computer, to a cellular telephone, to a handgun, and other such personal devices typically require an authorization database of just a few people.

Biometric identification and verification are useful in many applications. Examples include verifying identity prior to activating machinery or gaining entry to a secure area. Another example would be identification for matching an individual to records on file for that individual, such as for matching hospital patient records when the individual's identity is unknown. Biometric identification is also useful to match police records at the time a suspect is apprehended, but true identity of the suspect is not known. Additional uses of biometric identification or verification include automotive keyless start and entry applications, secure computer and network access, automated financial transactions, authorized handgun use, and time-and-attendance applications.

Current methods for biometric identification are manifold, but some of the most common techniques include fingerprint pattern matching, facial recognition, hand geometry, iris scanning, and voice recognition. Each of these technologies addresses the need for biometric identification to some extent. However, due to cost, performance, or other issues, each of the existing methods has advantages and disadvantages relative to the other technologies.

One present biometric product on the market is known as the LiveGrip™, made by Advanced Biometrics, Inc. This product is based on the technology disclosed in U.S. Pat. No. 5,793,881, by Stiver et al. In this patent, Stiver et al. disclose an identification system that is a security device, which consists of a cylindrical or elongated transparent shell with an internal light source and a means to scan the hand of the person grasping the shell to record the internal structure or subcutaneous structure of the hand using an imaging methodology. The system uses near-infrared light to image the pattern of blood vessels and associated tissue in the hand. The LiveGrip product based on this patent is claimed to have reduced the ability for an intruder to fool the biometric system as they claim can be easily done using a latex mold with many finger print readers or hand-geometry systems. However, the imaging approach requires good quality optics and/or detector arrays that add to both system complexity and cost. Further, the system relies on imaging blood vessels, and therefore, requires that the same site be presented to the system in use as during enrollment and further requires that the repositioning of the site is accurate enough to allow the software to align the two images to confirm identity. Finally, the size of the sensor head is limited to the portion of the hand that must be imaged for accurate identification.

Others in the field have disclosed methods and systems for measuring properties of samples based on an optical nonlinearity associated with the depletion of the density of states that depends on the presence and magnitude of multiple simultaneous wavelengths of illumination light. In some cases these nonlinear optical spectroscopic sensors are mounted on linear potentiometers and are adjusted to measure the optical properties of the tissue between consecutive pairs of fingers. The resulting measurements from potentiometers are combined with the measurements from the nonlinear optical probes to act as inputs into an identification process.

Living human tissue is recognized as a dynamic system containing a multitude of components and analyte information that is particularly useful in the medical profession for diagnosing, treating and monitoring human physical conditions. To this end, effort has been directed toward developing methods for non-invasive measurement of tissue constituents using spectroscopy. The spectrographic analysis of living tissue has been focused on the identification of spectral information that defines individual analytes and relates such spectral data to the analyte's concentration. Concentrations of these analytes vary with time in an individual person. Acquiring tissue spectral data with sufficient accuracy for use in diagnosis and treatment has proven difficult. Difficulties in conducting the analysis have been found that are related to the fact that the tissue system is a complex matrix of materials with differing refractive indices and absorption properties. Further, because the constituents of interest are many times present at very low concentrations, high concentration constituents, such as water, have had a detrimental impact on identifying the low level constituent spectral information and giving an accurate reading of the desired constituent concentration. Development of these techniques has always focused on the changes in spectral output with change in concentration of a dynamic analyte of interest, such as glucose. The techniques disclosed are focused on identifying concentrations of specific analytes, the concentration of which is expected to vary with time.

Improved methods and apparatus for gathering and analyzing a near-infrared tissue spectrum for an analyte concentration are disclosed in the following U.S. Patent applications and issued patents, each of which is incorporated herein by reference in its entirety: U.S. Pat. Nos. 5,655,530 and 5,823,951 relate to near-infrared analysis of a tissue analyte concentration that varies with time, with a primary focus on glucose concentrations in diabetic individuals; U.S. Pat. No. 6,152,876 discloses additional improvements in non-invasive living tissue analyte analysis.

U.S. Pat. No. 5,636,633, the entire disclosure of which is incorporated herein by reference, relates, in part, to another aspect of accurate non-invasive measurement of an analyte concentration. The apparatus includes a device having transparent and reflective quadrants for separating diffuse reflected light from specular reflected light. Incident light projected into the skin results in specular and diffuse reflected light coming back from the skin. Specular reflected light has little or no useful information and is preferably removed prior to collection. U.S. Pat. No. 5,935,062, the entire disclosure of which has been incorporated herein by reference, discloses a further improvement for accurate analyte concentration analysis which includes a blocking blade device for separating diffuse reflected light from specular reflected light. The blade allows light from the deeper, inner dermis layer to be captured, rejecting light from the surface, epidermis layer, where the epidermis layer has much less analyte information than the inner dermis layer, and contributes noise. The blade traps specular reflections as well as diffuse reflections from the epidermis.

U.S. Pat. No. 5,435,309, the entire disclosure of which is incorporated herein by reference, relates to a system for selecting optimal wavelengths for multivariate spectral analysis. The use of only one wavelength gives insufficient information, especially for solutions having multiple components. The use of too many wavelengths can include too much noise and lead to combinatorial explosion in calculations. Therefore, the number of wavelengths used should be limited and the wavelengths well chosen. Genetic algorithms are used in this reference to select the most fit wavelengths.

BRIEF SUMMARY OF THE INVENTION

Embodiments of the invention provide method and systems for performing biometric identifications that avoid some deficiencies of the prior art. Some of these embodiments make use of a linear spectroscopic analysis that permits an unexpectedly simple and reliable technique for performing the biometric identifications. Some embodiments are generally applicable to a wide range of biometric tasks, which include identifying individuals (either humans or animals), verifying purported identities of individuals, verifying the liveness of tissue, as well as providing or denying access on the basis of such assessments.

Thus, in a first set of embodiments, a method is provided for identifying an individual. Electromagnetic radiation is propagated into tissue of the individual. A measured spectral variation is received in the form of electromagnetic radiation scattered from the tissue of the individual. The received radiation may thus be reflected by or transmitted through the tissue, or combinations thereof. The measured spectral variation is compared with a previously stored spectral variation over a predetermined wavelength interval. The wavelength interval may alternatively be defined in terms of a frequency interval or any other equivalent measure. The comparison is performed at each of a plurality of wavelengths within the predetermined wavelength interval and is performed of a property of the measured and previously stored spectral variations that is independent of a presence of other wavelengths. The individual is designated as having an identity associated with the previously stored spectral variation if the measured spectral variation is consistent with the previously stored spectral variation.

In some embodiments, the property is an amplitude of the measured and previously stored spectral variations at each of the plurality of wavelengths. In such instances, the comparison may be performed by calculating a discriminant spectral variation at each of the plurality of wavelengths from the measured and previously stored spectral variations at the each of the plurality of wavelengths. The discriminant spectral variation may correspond, for example, to a wavelength-by-wavelength difference of the measured and previously stored spectral variations. Alternatively, the discriminant spectral variation may correspond to a wavelength-by-wavelength ratio of the measured and previously stored spectral variations. Comparing the measured spectral variation with the previously stored spectral variation may further comprise determining whether the discriminant spectral variation is consistent with a calibration database of intraperson difference spectra substantially lacking in interperson spectral differences. In one embodiment, the calibration database comprises spectral differences derived from a plurality of combinations of spectral variations over different conditions from a single individual.

Propagating the electromagnetic radiation into the tissue of the individual may comprise propagating a broad spectral band or may comprise propagating a plurality of signals having different wavelength characteristics. In one embodiment, a time-varying sequence of wavelengths is propagated.

Designating the individual as having an identity associated with the previously stored spectral variation may take place in different ways in different embodiments. For example, in one instance, a purported identity of the individual is obtained, and the previously stored spectral variation corresponds to a spectral variation associated with the purported identity. In such instances, designating the individual as having the identity associated with the previously stored spectral variation thereby corresponds to verifying the purported identity of the individual. In other instances, the previously stored spectral variation may be comprised by a plurality of previously stored spectral variations, with the comparison comprising comparing the measured spectral variation with each of the plurality of previously stored spectral variations. In such instances, the identification may be performed without any input from the individual other than the biometric measurement.

In another set of embodiments, a method is provided for implementing a biometric task with respect to an individual. A spectral variation of electromagnetic radiation is measured from subepidermal tissue from at least one site of the individual. A linear spectroscopic analysis is performed of the spectral variation. The biometric task is performed in accordance with a result of the linear spectroscopic analysis. Performing the biometric task may comprise performing a comparison with a database to identify the individual.

There are a variety of sites that are particularly suitable. For example, in one embodiment, the at least one site comprises at least one of a dorsal and ventral surface of a proximal phalange of a finger or thumb of the individual. In another embodiment, the at least one site comprises at least one of a dorsal and ventral surface of a medial phalange of a finger of the individual. In a further embodiment, the at least one site comprises at least one of a dorsal and ventral surface of a distal phalange of a finger or thumb of the individual. In another embodiment, the at least one site comprises at least one of a dorsal and ventral surface of a wrist of the individual. In still a further embodiment, the at least one surface comprises a web between an index finger and thumb of the individual. In yet another embodiment, the at least one surface comprises a thenar eminence of the individual. In a further embodiment, the at least one site comprises a hypothenar eminence of the individual. In a different embodiment, the at least one site comprises a medial hypothenar eminence of the individual.

The methods of the invention may be embodied in a system. The apparatus includes a source of electromagnetic radiation adapted to propagate radiation into tissue of the individual, as well as a receiver adapted to receive a measured spectral variation in the form of electromagnetic radiation scattered from the tissue of the individual. A spectral-variation database is also provided with a previously stored spectral variation. A computer-readable storage medium is coupled with a processor, the computer-readable storage medium having a computer-readable program embodied therein for directing operation of the processor. The computer-readable program includes instructions for operating the apparatus to identify an individual in accordance with the embodiments described above.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components.

DETAILED DESCRIPTION OF THE INVENTION

1. Overview

Figure 1:
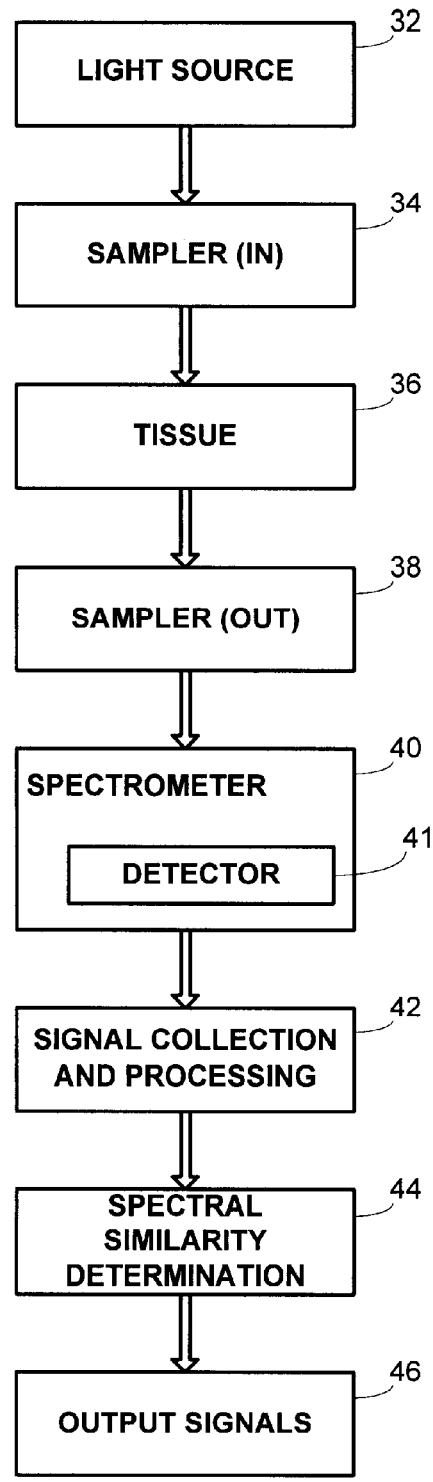
FIG. 1 is a block diagram of components incorporated into an embodiment of a biometric analyzer.

Detailed embodiments of the present invention are disclosed herein. However, it is to be understood that the disclosed embodiments are merely exemplary of the present invention, which may be embodied in various systems. Therefore, specific details disclosed herein are not to be interpreted as limiting, but rather as a basis for the claims and as a representative basis for teaching one of skill in the art to variously practice the invention.

Embodiments of the present invention are based on the inventors' recognition that an accurate, precise and repeatable tissue spectrum of an individual in the near ultraviolet range, visible range, very near infrared, near infrared range and combinations of these ranges contains spectral features and combinations of spectral features which are unique to that individual. In certain embodiments, linear spectroscopic principles are used. The use of linear spectroscopic principles may simplify the instrumentation complexity and cost for performing the spectroscopic measurements relative other more elaborate spectroscopic techniques that rely on nonlinear optical properties of the tissue. Throughout this disclosure, spectral data spanning the near-ultraviolet, visible and very near-infrared regions from 350 nm to 1000 nm will be referred to as "silicon-region data" due to the fact that this is substantially the spectral region over which silicon detectors are sensitive. Data collected in the spectral region beyond 1000 nm is referred to herein as "infrared data."

Embodiments of the present invention are further based on a recognition by the inventors that proper analysis, utilizing discriminant analysis techniques, neural networks, and other forms of multivariate analysis, can identify these unique features or combinations, which are not readily apparent in visual analysis of a spectral output, so that an individual's identity may be verified by comparison of tissue spectral data taken at the time of verification compared to stored tissue spectral data from prior testing. The identification methods can also be used in conjunction, or simultaneously, with measurement of analyte concentrations in an individual. As well, the biometric methods of the present invention can be used in conjunction with other biometric techniques to either increase the accuracy of the system, or offer more than one method to identify a person in case one method is disabled due to system failure or other reason.

Prior spectral data may be used to train the device to identify a particular person based on features that are recognized unique to that particular individual. These unique spectral features have been found to be consistently present even though the tissue being analyzed at each time of analysis is a dynamic system which contains components and analytes whose concentration vary, with resulting tissue spectral variations, due to physiological changes in the individual.

Various advantages of the methods and apparatus disclosed herein will be evident to those of skill in the art. For example, some biometric identification devices have the distinct disadvantage of requiring the use of specific body parts in order to achieve their techniques. For example, fingerprint devices require that only the extreme ventral portion of the fingers can be used as the biometric site. The methods and apparatus of the present invention enable biometric identification to occur with finger, palms, wrists, forearms and other convenient sites on the body. Further, even in the case of using fingers, the present invention allows use of multiple sites along the finger on both the dorsal or ventral surfaces. Present finger print readers require that the same finger be presented to the reader for identification or verification that was presented during the enrollment analysis. The present invention can use different fingers (or other sites) for enrollment and for subsequent verification. This capability provides for increased enrollment efficiency since the user only has to present one enrollment site to the system, but also provides critical flexibility during the use of the device. An example of this flexibility is the case where the user has enrolled a site on a particular hand and that particular site is unavailable for subsequent analysis due to some injury or some severe surface contamination of the site. This spectroscopic-based biometric system of the present invention can operate on the site from the other hand without previous enrollment of such site.

The inventors have been able to demonstrate that the near infrared spectral data in the range from 1.25–2.5 $\mu$m as collected with a near-infrared spectroscopic system can be used for spectral biometric determinations of identity or verification of identity. As well, the inventors have also shown that near-ultraviolet, visible and very near-infrared spectral data in the range from 350–1000 nm can also be used to perform biometric determinations. Although either or both of the aforementioned spectral regions can be used, the latter region may be advantageous due to the lower cost and generally higher performance of the silicon detectors that can be incorporated in systems operating in this spectral region.

In some embodiments, performance of the device and algorithms described herein are optimized for the performance of biometric tasks. Accordingly, the inventors have been able to achieve high accuracy rates with the techniques disclosed herein, even though the tissue being analyzed is a dynamic system with analyte concentrations, and thus, tissue spectral data, varying considerably over time and between analysis. Success of the method of the present invention is believed tied to two components.

First, the method incorporates an apparatus and technique for accurately and repeatably acquiring a tissue spectrum that minimizes effects due to instrumental, environmental and sampling changes, while remaining sensitive to slight changes in the spectral properties of tissue at any given wavelength. The system optimizes optical throughput both into and out of the tissue sample. Second, because the spectral features or combinations of spectral features that are unique for a particular individual are not readily apparent or identified by visual comparison of a spectral result, embodiments of the present invention use discriminant analysis techniques to first train the device to identify spectral features of significance for the individual and then compare such features to new spectral data at the time of attempted identification or verification. Embodiments of the present invention incorporate discriminant analysis methods such as those based upon Mahalanobis distances, spectral residual magnitudes, K-nearest-neighbor methods, or linear or nonlinear discriminant techniques to compare spectral data acquired from an individual with spectral data present in a database.

Embodiments of the present invention, thus, include a method for identifying or verifying the identity of an individual using non-invasive tissue spectroscopy. Depending on the tissue site and the wavelength range, the spectral data may be collected in a transmission or reflectance configuration. One method and apparatus illuminates skin with selected radiation and collects the reflected, non-absorbed selected radiation. Diffuse, rather than specular, reflected light is preferably collected, such as light diffusely reflected from the dermis or other tissue deeper than the epidermis. The spectral data collected can be stored in a computer database.

In some embodiments, the methods of the present invention are based on an analysis of linear spectroscopic phenomena. In particular, in such analysis, the magnitude of the light measured at a particular wavelength after passing through the sample is treated as independent of the presence or amount of other wavelengths of light present. In such embodiments, the algorithms used consider the relative amplitudes of different wavelengths of light but do not require steps to estimate, isolate or use any optical nonlinearities that may be present in the sample being measured. In other embodiments, such a linear-spectroscopic analysis may also be combined with a nonlinear-spectroscopic analysis.

In most materials, and in particular in skin, optical nonlinear effects are very small relative to the linear portion of the effects. As such the presence of small optical nonlinearities do not typically affect the accuracy of the biometric measurement systems in embodiments that rely on a linear-spectroscopic analysis. For this reason, such embodiments are equally applicable to a range of illumination options—including illuminating the sample using a series of individual wavelengths of light, illuminating with a plurality of wavelengths of light simultaneously, or illuminating with multiple subsets of wavelengths of light (e.g. encoding using Hadamard codes, Fourier modulation or other methods). The choice of illumination method in the present invention can be made based on the requirements of the system and the sensor components, rather than to achieve a particular illumination sequence that might otherwise be necessary to isolate certain optical characteristics of the sample.

In some embodiments, three major data elements may be identified: calibration, enrollment and target spectral data. The calibration data are used to establish spectral features that are important for biometric determinations. This set of spectral data comprises a series of tissue optical spectral data that are collected from an individual or individuals of known identity. Preferably, these data are collected over a period of time and a set of conditions such that multiple spectra are collected on each individual while they span nearly the full range of physiological states that a person is expected to go through. As well, the instrument or instruments used for spectral collection could also span the full range of instrumental and environmental effects that it or sister instruments are likely to see in actual use. These calibration data may then be analyzed in such a way as to establish spectral wavelengths or "factors" (i.e. linear combinations of wavelengths or spectral shapes) that are sensitive to between-person spectral differences while being insensitive to within-person effects as well as instrumental effects (both within- and between-instruments) and environmental effects. These wavelengths or factors may then be used subsequently to perform the biometric determination tasks.

The authorization or enrollment spectra may be collected from individuals who are authorized or otherwise required to be recognized by the biometric system. Enrollment spectra can be collected over a period of seconds or minutes. Two or more optical samples can be collected from the individual to ensure similarity between the samples and rule out a sample artifact in one of the samples. If such an artifact is found, additional enrollment spectra can be collected. These spectral data can either be averaged together or otherwise combined, or stored separately. In either case, the data are stored in an enrollment database. In most cases each set of enrollment data is linked with an identifier for the persons on whom the spectra were measured. In the case of an identification task, the identifier can be used for record keeping purposes of who accessed the biometric system at which times. For a verification task, the identifier is used to extract the proper set of enrollment data against which verification is performed.

The target spectral data correspond to spectral data collected when a person attempts to use the biometric system to identify them or verify their identity. They may be compared to the appropriate enrollment spectrum or spectra using the classification wavelengths or factors determined from the calibration set to determine the degree of similarity. If the target and enrollment spectra are sufficiently similar, the biometric determination is made. If the similarity is inadequate, then the biometric determination is cancelled and a new target measurement may be attempted. In the case of identification, the system compares the target spectrum to all of the enrollment spectra and reports a match if one or more of the enrolled individual's data is sufficiently similar to the target spectrum. If more than one enrolled individual matches the target, then either all of the matching individuals can be reported, or the best match can be reported as the identified person. In the case of verification, the target spectrum is accompanied by a purported identity that is collected using a magnetic card, a typed user name, a transponder, a signal from another biometric system, or other means. This identifier is then used to retrieve the corresponding set of spectral data from the enrollment database, against which the biometric similarity is made and the identity verified or denied.

In a particular set of embodiments, a liveness determination is made to verify that the tissue being analyzed is living tissue. Such a determination may be considered to be a special case of identifying a correspondence between the target spectral data and a plurality of enrollment spectra, with the correspondences sharing the property of being derived from living tissue. In some applications, the liveness determination by itself is sufficient. In other embodiments, the liveness determination may be combined with other identification methods, including some biometric identification methods. Such hybrid systems may be suitable, for example, in applications where equipment already exists for using an existing biometric method, but where there is a concern that that method may be circumvented by using nonliving tissue.

In one method of verification, principal component analysis may be applied to the calibration data to generate spectral factors. These factors may then be applied to the spectral difference taken between a target spectrum and an enrollment spectrum to generate Mahalanobis distance and spectral residual magnitude values as similarity metrics. Identify is verified only if the aforementioned distance and magnitude are less than a predetermined threshold set for each. Similarly, in one method for biometric identification, the Mahalanobis distance and spectral residual magnitude are calculated for the target spectrum relative each of the database spectra. Identify is established as the person or persons associated with the database spectra that gave the smallest Mahalanobis distance and spectral residual magnitude that is less than a predetermined threshold set for each.

One system for performing biometric tasks in an embodiment includes: a computer having an input device and an output device; a database including selected tissue spectral data for enrolled persons; a radiation or light source for projecting selected radiation into sub-epidermal tissue; a sampler to interface with tissue; a spectrometer including a detector for measuring subcutaneous radiation intensity over a plurality of wavelengths; and a classification program running in the computer for assessing the degree of similarity between the a plurality of optical spectra by applying a set of classification factors. The program can include software for performing discriminant analysis. As well, the program can include a separate module to collect additional authorized spectral data or to remove existing spectral data from the database. In the case of using the spectral biometric system for verification tasks, the system will also include some means of establishing the purported identity of the person attempting to gain access. Methods to collect the purported identity include, but are not limited to, magnetic cards, PIN code, keyboard entry of the name or ID, voice command, transponder, etc.

2. Spectral Acquisition

As previously stated, there are two components that are exploited in embodiments of the invention. First, certain embodiments incorporate an apparatus and technique for accurately and repeatably acquiring a tissue spectrum that minimizes effects due to instrumental, environmental and sampling changes, while remaining sensitive to slight changes in the spectral properties of tissue at any given wavelength. As well, the system may optimize optical throughput both into and out of the tissue sample. Second, the method may use specific techniques for training the instrument to identify spectral features of significance for a particular individual, and then to compare such features to new spectral data acquired at the time of attempted verification or identification. Because the spectral features or combinations of spectral features that are unique for a particular individual are not readily apparent or identified by visual comparison of a spectral result and the unique spectral features are present at different wavelengths for different individuals, the present invention may use discriminant analysis techniques to compare spectral data. Each component of the apparatus and method of the present invention are detailed below.

Referring now to FIG. 1, a block diagram of an overall spectroscopic system in accordance with an embodiment of the present invention is shown. The system generally includes a light or energy source 32 that provides light energy and selected wavelengths to the input side of an optical sampler 34. The light passes from the input of the sampler 34 into the tissue 36. Once in the tissue 36, a portion of the light passes into the output side of the sampler 38, which then enters a spectrometer 40. The signal collected by the detector 41 in the spectrometer 40 is digitized and sent to a processing subsystem 42 with the data analyzed within a spectral similarity determination subsystem 44, which in turn provides the proper output 46 based on the data. The output may simply be a yes or no determination of whether a person is who they allege to be or, alternatively, the system may output an identification of an unknown individual.

In acquiring tissue spectral data, measurements can be made in at least two different modes. It is recognized that one can measure light transmitted through a section of tissue, or one may measure light reflected from tissue. Although light in such regions as the silicon-region can penetrate tissue to significant depths of one centimeter or more, depending upon the wavelength, transmission sampling of the tissue limits the region of the body that can be used. Thus, while either mode of sampling is applicable to embodiments of the present invention, and especially to analysis utilizing light in the silicon-region, a preferred and more versatile sampling method is based upon reflected light.

Photons reflect and refract at refractive index discontinuities, and so light impinging on tissue immediately has a small reflectance at the tissue surface. This is referred to as specular reflectance. Since this light does not penetrate into the tissue, it contains little information about the tissue constituents. This is especially true in light of the physiology of skin, which possesses an outward layer which is essentially dead and lacks spectral information believed unique to an individual. Thus, reflected light energy containing spectral data unique to an individual is believed to be that light which is reflected back to the surface through refractive index discontinuities deeper within the tissue sample. This reflected light energy is referred to as diffusely reflected light.

In FIG. 1, the spectrometer subsystem 40 can include a variety of methods and apparatus. One method of detecting optical spectra is achieved based upon optical interference phenomena such as in a Fourier transform infrared spectrometer system. One such system is disclosed in U.S. patent application Ser. No. 09/832,585 entitled "System for Noninvasive Measurement of Glucose in Humans," filed Apr. 11, 2001, and U.S. patent application Ser. No. 09/832,631 entitled "Encoded Variable Filter Spectrometer," filed Apr. 11, 2001, the disclosures of which are both incorporated herein by reference. Other ways to detect optical spectra include using gratings, prisms, tunable filters, mock interferometers, Sagnac or common-path interferometers, and other means known to those of skill in the art. Many of these spectrometers also enable the spectrometer and detector to be treated as two distinct units with the spectral-separation occurring prior to the tissue. For example, an FTIR, a tunable filter, or a mock interferometer could all be placed prior to the tissue and impress an encoding on the light, which will subsequently be seen by the detector placed after the tissue as shown in FIG. 1.

The light or energy source 32 shown in FIG. 1 can be selected from many available designs. In one embodiment, a wide band source is utilized with optical wavelengths emitted from the light or energy source 32 between 1000 nm and 2.5 $\mu$m. The light or energy source 32 can alternatively comprise a light source emitting light in the silicon-region of the spectrum, which is defined as the spectral range over a silicon detector is active and is roughly between 350 and 1000 nm. Light sources can be based upon quartz tungsten halogen incandescent bulbs, broad-band light emitting diodes (LEDs), globe bars, or a variety of other optical sources known in the art.

In practicing embodiments of the present invention, the tissue spectral data may be determined by measuring the light intensity received by the output sensor at the various wavelengths which give indications of the absorption at such wavelengths of the infrared energy as a function of the composition of the tissue sample. As is well known in the art, a spectrometer 40 is able to convert the intensity of the optical energy incident on the detector into a proportional amplitude of voltage, current or other signal. In this way, an output spectrum is defined for the tissue under analysis.

The light or energy source 32 and spectrometer 40 can alternatively be replaced by a collection of narrow-band optical sources such as light emitting diodes (LEDs) laser diodes (LDs), vertical cavity surface emitting lasers (VCSELS), or a set of optically filtered sources that collectively span a range of wavelengths. The narrow-band sources can be turned on individually and measurements taken by the detector 41, in which case the spectrometer 40 is optional since the detected light is known to be coming from a particular narrow-band source. Equivalently, the collection of narrow band sources can also be illuminated in an encoded or modulated fashion such as Hadamard, Fourier or other similar methods.

Figure 2A:
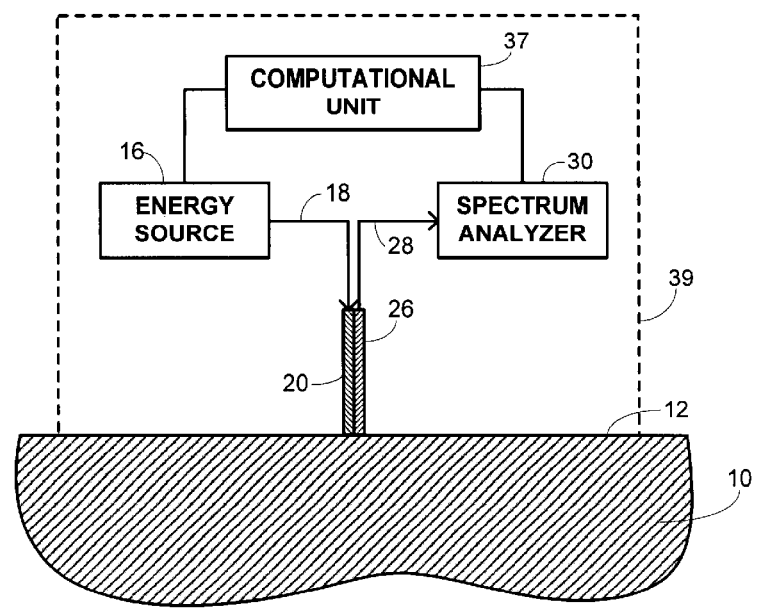
FIG. 2A is a partial cross-sectional view of a sensor element coupled to the skin surface via an indexing-matching fluid.
Figure 2B:
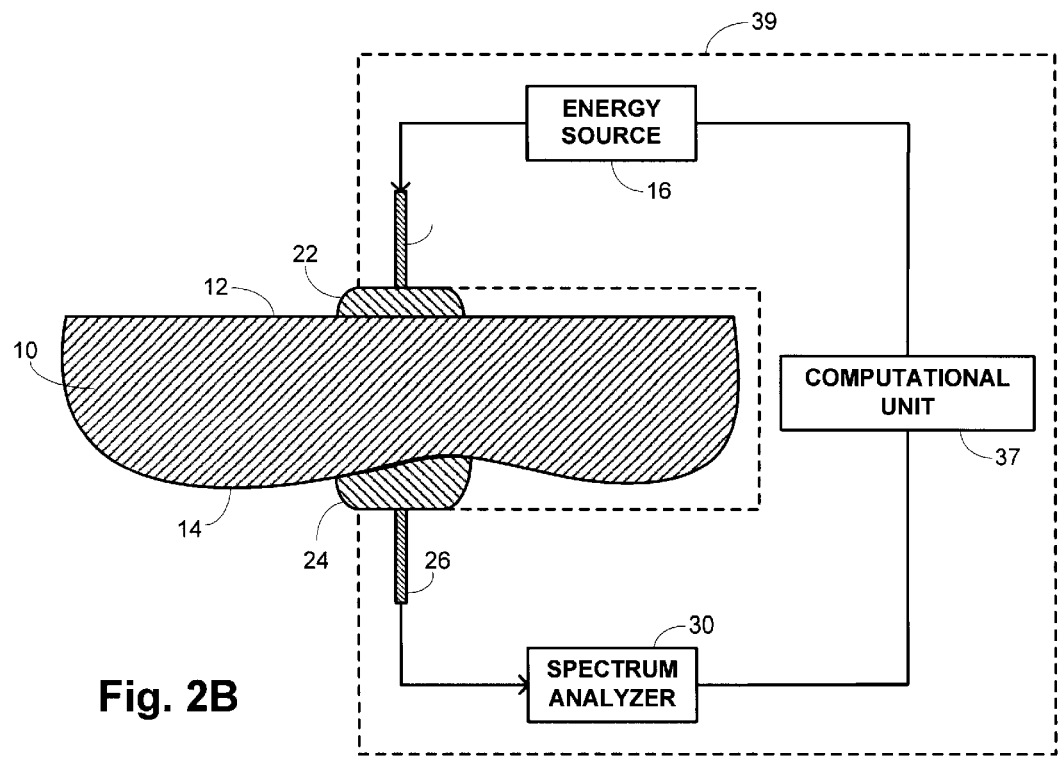
FIG. 2B is a partial cross-sectional view of an alternative embodiment of a sensor element coupled to opposite sides of a skin surface via an indexing-matching fluid.

Now referring to FIGS. 2A and 2B, partial cross-sectional views of two embodiments of an apparatus for acquiring a tissue spectrum are depicted. In FIG. 2A, the optical illumination path 18 and the optical collection path 28 are on the same surface of the skin surface 12 and underlying tissue 10. This optical sampling configuration is referred to as diffuse reflectance. FIG. 2B shows an alternative arrangement where the optical illumination path 18 and optical detection path 28 are on opposite sides of a piece of tissue 10 and surrounding skin 12. This optical configuration is referred to as an optical transmission geometry. It is well suited for relatively thin portions of the body such as the webs between the fingers, the fingers themselves, earlobes, and other areas that light can pass through in some measurable amount.

In either configuration, the apparatus used to convey the light into and out of the skin 12 and underlying tissue 10 is referred to as a sampler 39. The sampler 39 may comprise optical fibers 20, 26 to deliver the light to the proper location on the tissue as shown in FIGS. 2A and 2B. The energy source 16 is operatively coupled to a first element for transmitting energy 18 from the energy source 16 to the input element 20. In one embodiment, this first element may correspond simply to the transmission of light energy to the input element 20 through air by placing the energy source 16 proximate the input element 20.

The input element 20 of the sampler 39 can include optical fibers or an optical lens which focuses the light energy to a high energy density spot. However, it is understood that other beam focusing means may be utilized in conjunction with the optical lens to alter the area of illumination. For example, a multiple lens system, tapered fibers, or other conventional optical beam-shaping devices could be utilized to alter the input light energy.

In other embodiments, the sampler 39 can be of a non-fiber design comprising a compound parabolic concentrated (CPC) to concentrate the light at the sample site, as disclosed in the above cited U.S. patent application Ser. No. 09/832,631, the entire disclosure of which has been incorporated by reference. Once the light interacts with the tissue, it can be collected in a manner similar to the illumination methods. An appropriate arrangement of optical fibers can be used, or a non-fiber collection device such as a CPC may be employed.

In both embodiments depicted in FIGS. 2A and 2B, an output sensor 26 may be utilized to receive reflected or transmitted light energy from the tissue 10. In one embodiment, a specular control device is incorporated to separate the specular reflected light from diffusely reflected light. All such methods and devices provide an optical separation between the illumination light and the region of skin where light is detected in order to ensure that detected light passed through skin 12 and underlying tissue 10 before being detected. Some specular control devices are disclosed in U.S. Pat. No. 5,935,062, the disclosure of which has been incorporated herein by reference. As described in conjunction with a method of analysis below, the embodiment of FIG. 2A has an output sensor 26 which receives reflected light energy, while the embodiment of FIG. 2B includes an output sensor 26 which receives transmitted light through the tissue 10. As with the input element 20, the output element 26 comprise an optical lens. Other optical collection means may be incorporated into an output element 26, such as a multiple lens system, tapered fiber, or other beam-collection means to assist in directing the light energy to the spectrum analyzer 30.

A second element for transmitting energy 28 is operatively connected to the output element 26. The light transmitted through the second element for transmitting energy 28 is transmitted to the spectrum analyzer 30. In one embodiment, the operative connection to the output element 26 includes transmission of the reflected or transmitted light energy exiting the output element through air to the spectrum analyzer 30. A mirror or series of mirrors may be utilized to direct this light energy to the spectrum analyzer.

Figure 3:
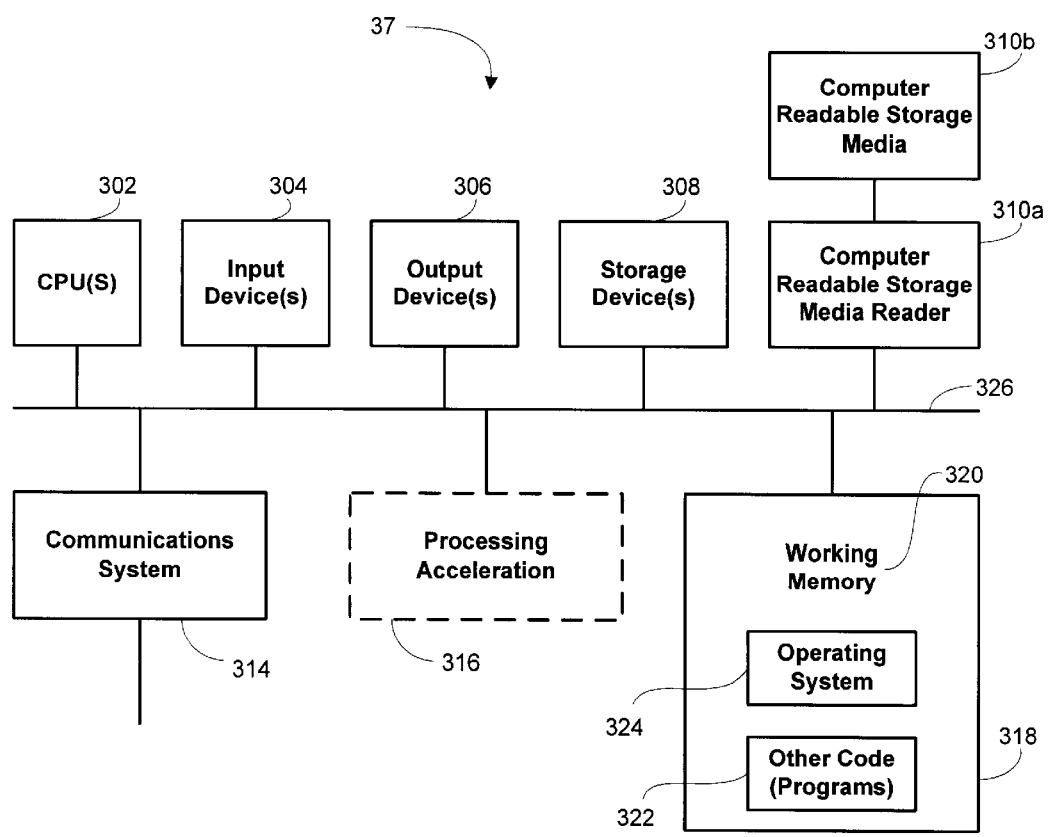
FIG. 3 is a schematic illustration of a computational system on which methods of the invention may be embodied.

Operation of the energy source 16 and the spectrum analyzer 30 comprised by the sampler 39 may be coordinated by a computational unit 37. FIG. 3 provides a schematic illustration of a structure that may be used to implement the computational unit 37. FIG. 3 broadly illustrates how individual system elements may be implemented in a separated or more integrated manner. The computational unit 37 is shown comprised of hardware elements that are electrically coupled via bus 326, including a processor 302, an input device 304, an output device 306, a storage device 308, a computer-readable storage media reader 310a, a communications system 314, a processing acceleration unit 316 such as a DSP or special-purpose processor, and a memory 318. The computer-readable storage media reader 310a is further connected to a computer-readable storage medium 310b, the combination comprehensively representing remote, local, fixed, and/or removable storage devices plus storage media for temporarily and/or more permanently containing computer-readable information. The communications system 314 may comprise a wired, wireless, modem, and/or other type of interfacing connection and permits data to be exchanged with the sampler 39 to implement embodiments of the invention. The storage device 308 may be used, for example, to maintain a copy of the databases described below and used in implementing embodiments of the invention. Alternatively, such databases may be stored externally to the sampler 39, with the communications system 314 being used to access data from the databases as necessary in implementing embodiments of the invention.

The computational unit 37 also comprises software elements, shown as being currently located within working memory 320, including an operating system 324 and other code 322, such as a program designed to implement methods of the invention. It will be apparent to those skilled in the art that substantial variations may be made in accordance with specific requirements. For example, customized hardware might also be used and/or particular elements might be implemented in hardware, software (including portable software), or both. Further, connection to other computational devices such as network input/output devices may be employed.

In practicing methods of the present invention, a tissue 10 area is selected as the point of analysis. In developing the embodiments described in connection with FIGS. 2A and 2B, it initially appeared to the inventors that there should be no a priori restriction on the point of analysis, but subsequent experimental investigations revealed that some tissue areas provide greater reliability than others. For example, the forearm of an individual has been found to provide particularly reliable results, as has the thenar eminence, certain portions of a finger or thumb, and the wrist. Reliable results may be obtained from either the dorsal or ventral surfaces of the fingers and thumbs, and from either the dorsal or ventral surfaces of the wrist. Other sites that provide reliable results include the web between the thumb and index finger, the hypothenar eminence, the medial hypothenar eminence, the earlobe, and the temple, although more generally any skin surface may be used.

The inventors believe that the particular suitability of some sites derives from a improved ability to ensure good optical coupling between the skin surface and the sampler 39. Such effective optical coupling is itself believed to result from the ergonomic amenability of those sites to such a sampler design, and also from constraints that those sites provide on blocking specular light. Preferably, the area for sampling is a relatively smooth, uncalloused surface, although the inventors have found good reliability even with rough skin surfaces. Optionally, a quantity of optical-coupling or index-matching medium, whether fluid or deformable solid, can be placed on the skin surface 12 in the area to be analyzed to couple the sampler 39.

In acquiring spectral data of the tissue 10, light energy from the energy source 16 is transmitted through the first element for transmitting infrared energy 18 into the input element 20. The light energy is transmitted from the input element 20 to the skin surface 12, perhaps through the index-matching medium if it is used. The light energy contacting the skin surface 12 is differentially absorbed by the various components and analytes contained below the skin surface 12. In one embodiment, the non-absorbed light energy is reflected back to the output element 26, perhaps propagating again through the index-matching medium if it is used. The non-absorbed light energy is transmitted via the second element for transmitting infrared energy 28 to the spectrum analyzer 30.

In the alternative embodiment of FIG. 2B, the index-matching medium is shown explicitly, but need not necessarily be included. The light energy propagated through the input element 20 and first quantity of index-matching medium 22 is differentially absorbed by the tissue 10, while a quantity of the light energy at various wavelengths is transmitted through the tissue 10 to the opposing or second skin surface 14. From the second skin surface 14, the non-absorbed light energy is propagated through the second quantity of index-matching medium 24 to the output element 26 with subsequent propagation to the spectrum analyzer 30 for producing the tissue spectrum. Tissue sites that can be used for transmission sampling are similar to those described above, but preferably not so thick as to make it difficult for light to penetrate through the tissue. Accordingly, suitable sites include fingers and thumbs, the web between the thumb and index finger, the earlobe, or any other skin surface surrounding a relatively thin portion of the anatomy. Preferably, the area for sampling is a relatively smooth, uncalloused surface, although good results have also been obtained using rougher surfaces as sites.

3. Biometric System Procedures

Once accurate and repeatable spectral data for tissue analysis is acquired, a methodology may be defined for training the device or instrument to identify spectral features or combinations of features that are unique for that particular individual and then to compare the database's spectral data and its unique features to new spectral data from supposedly the same individual to determine whether or not the spectral data in fact came from the same individual.

In one embodiment, the identification or verification task is implemented when a person seeks to perform an operation for which there are a limited number of people authorized (e.g., perform a spectroscopic measurement, gain entry into a room, achieve control over an interlocked vehicle or piece of machinery, pass through an immigration checkpoint, etc.). The person's spectral data is used for identification or verification of the person's identity. In this embodiment, the person initially enrolls in the system by collecting one or more representative tissue spectra. If two or more spectra are collected during the enrollment, then these spectra may be checked for consistency and recorded only if they are sufficiently similar, limiting the possibility of a sample artifact corrupting the enrollment data. For a verification implementation, an identifier such as a PIN code, magnetic card number, username, badge, voice pattern, other biometric, or some other identifier could also be collected and associated with the confirmed enrollment spectrum or spectra.

In subsequent use, biometric identification would take place by collecting a spectrum from a person attempting to gain authorization. This spectrum would then be compared to the spectra in the enrolled authorization database and an identification made if the match to an authorized database entry was better than a predetermined threshold. The verification task is similar, but has the person present the identifier in addition to a collected spectrum. The identifier would then be used to select a particular enrollment database spectrum and authorization would be granted if the current spectrum was sufficiently similar to the selected enrollment spectrum. If the biometric task is associated with an operation for which only a single person is authorized, then the verification task and identification task are the same and both simplify to an assurance that the sole authorized individual is attempting the operation without the need for a separate identifier.

4. Data Processing and Algorithmic Details

In many embodiments, implementations of the proposed verification methodology generate a discriminant spectral variation, $D(v)$, using the spectrum just collected from the person wishing authorization, $V(v)$, and the enrolled authorized spectrum, $A(v)$ or spectra corresponding to the person whose identification was stated. For example, the discriminant spectral variation could correspond to a difference spectrum between $V(v)$ and $A(v)$:

$$D(v)=V(v)-A(v),\qquad\text{Equation 2}$$

where $v$ is a variable designating the spectral frequency or wavelength, and D, V, A are spectral values in absorbance units or some related quantities. Alternatively, D, V, and A could be spectral intensity values, and the discriminant spectral variation could be determined as an element-by-element ratio:

$$D(v)=V(v)/A(v)\qquad\text{Equation 3}$$

For identification, a procedure similar to the verification case is followed, but it is repeated for each entry in the enrollment database.

Other mathematical operations of a similar nature can alternatively be used for this application. For example, each of the operations described above provides an example determining a discriminant spectral variation at each wavelength from the values of measured and stored spectral variations at that wavelength. Such an analysis is invariant at each wavelength to the presence and amplitude of contributions at other wavelengths, and is accordingly an example of the linear spectroscopic analysis that is discussed in greater detail below.

In some embodiments, the analysis may be augmented through use of a spectral calibration dataset developed using the same mathematical operation as used for generating $D(v)$. The spectral differences (or ratio, etc.) in the calibration database are preferably formed from one or more people measured multiple times each. For robustness, the sampling of people included in the calibration database should span expected changes in the physiology, expected changes in or across the spectroscopic measurement devices, and changes in the measurement environment. In one embodiment, spectral differences can be generated in a multitude of combinations of spectra from a given person, but should never be formed using spectra from different people. By filling the calibration database with intra-person difference spectra, typical inter-person spectral differences are removed, and the resulting calibration database contains only intra-person spectral features as well as instrumental and environmental effects.

The verification task is accomplished through determining if the spectral difference, $D(v)$, is consistent with the calibration database. If the identification that the person stated is accurate, the resulting difference spectrum, $D(v)$, will contain only intra-person spectral features, and thus, be consistent with the calibration database. Conversely, if the identification is not accurate, $D(v)$ will contain inter-person spectral features and be incompatible with the intra-person spectral difference database for the individual. In this case, the verification will fail.

Similarly, identification is performed by comparing each of the difference spectra (one for each entry in the enrollment database) to the calibration database. Whichever difference(s) produces results that are consistent with the intra-person changes in the calibration database is (are) said to be the estimate of identity. If none of the differences produce results that are consistent with the calibration database, then the person attempting access is deemed to be an unauthorized intruder.

Consistency with the database can be ascertained in a variety of ways including linear discriminant analysis, quadratic discriminant analysis, K-nearest neighbors, neural networks, and other classification techniques. In some embodiments, discriminant analysis techniques based upon multivariate analysis techniques are used. These methods rely upon establishing the underlying spectral shapes (factors, loading vectors, eigenvectors, latent variables, etc.) in the intra-person calibration database, and then using standard outlier methodologies (spectral F ratios, Mahalanobis distances, Euclidean distances, etc.) to determine the consistency of $D(v)$ with the database. The underlying spectral shapes can be generated by multiple means as disclosed herein. First, the underlying spectral shapes can be generated based upon simple spectral decompositions (eigen analysis, Fourier analysis, etc.) of the calibration data.

In another embodiment, generating underlying spectral shapes is related to the development of a generic model as described in U.S. Pat. No. 6,157,041, entitled "Methods and Apparatus for Tailoring Spectroscopic Calibration Models," the entire disclosure of which is incorporated by reference. In this patent, the underlying spectral shapes are generated through a calibration procedure performed on intra-person spectral features.

In a further embodiment, the underlying spectral shapes may be generated by the development of a calibration based upon simulated constituent variation. The simulated constituent variation can model the variation introduced by real physiological or environmental or instrumental variation or can be simply be an artificial spectroscopic variation.

Those of skill in the art will recognize after reading this disclosure that still procedures for determining whether the spectral difference $D(v)$ is or is not consistent with the database can alternatively be applied to the identification and verification methods, and their use is intended also to be within the scope of the invention. These methods could be used either in conjunction with, or in lieu of the aforementioned techniques.

Many variations in the methodology are possible within the scope of the present invention. In one embodiment, the entire spectrum is stored at substantially even wavelength or wavenumber intervals. In another embodiment, only preselected wavelengths of likely interest are recorded. In yet another embodiment, the spectral data are analyzed and stored as parameters capable of substantially regenerating the various spectra. In this latter embodiment, measurements at specific wavelengths outside of the parameters are not stored. The enrollment spectra can be stored in a database. In one embodiment, a number of enrollment spectra are obtained at one sitting and used to populate the verified spectra database. In another embodiment, spectra are obtained over several sittings for an individual.

As previously stated, spectral differences or distances can be obtained by performing calculations on different measurements taken at the same wavelength for the same individual. Variations in defining the discriminant spectral variation are possible. The following discussion illustrates additional aspects of the application of a linear spectroscopic analysis in which measurement of one wavelength is substantially unrelated to the presence or magnitude of other wavelengths of illumination light due to optical interactions of a plurality of wavelengths in the material being measured. This illustration proceeds by sequentially considering the use of increasing numbers of wavelengths of illumination light, although it will be recognized that the invention is not limited to analysis using any particular number of wavelengths.

Consider first the case of measurement samples taken at a single wavelength. The spectral difference can take the form of a statistical analysis of the sample population, such as a mean measurement value and the standard deviation about the mean relative to a new spectral value at that wavelength. Various wavelengths can be evaluated in an attempt to maximize or minimize the standard deviation for the sample population. It may be desirable to select a wavelength to minimize the variation for that wavelength for samples taken for a single individual while maximizing inter-person variation, to allow for distinguishing or discriminating between the authorized person and an impostor. For example, a wavelength that did not vary between people would not be useful for biometric discrimination. At the same time, it is desirable to select a wavelength that does not also vary a great deal between measurements for the same individual, as the intra-person differences can swamp the interperson differences.

In the simple, single wavelength case discussed above, a wavelength could be selected that maximized inter-person spectral differences while minimizing intra-person spectral differences. In this one-dimensional example, a wavelength could be selected that tended to cluster the measurements for each individual tightly about a single point along an axis, while spreading these tight clusters along the axis for the numerous individuals. When a target sample is introduced, the measurement taken can be compared with the cluster of values for the individual for that purported identity. A threshold can be established for each cluster of values for a verified individual. For example, a threshold could be set at two standard deviations for the sample population, with any measurements falling outside of this range being rejected, and the target individual verification refused.

From the above simplified single wavelength example, the theory of analyzing the spectral data can be expanded. In a two-wavelength example, two wavelengths could be selected and the two wavelength measurements plotted against each other as X-Y coordinates in a two-dimensional plot. The X-Y plot could then show a series of clusters, each corresponding to different individuals measured multiple times, widely separated from each other. The spread of these clusters could be used to assess normal within person variation, and could be used to establish a probability value about the mean position of each cluster, such that a certain percentage of all measurements on a given person are expected to fall within a certain region around the mean cluster position.

When enrollment data are taken in the two-wavelength case, the position of each enrolled person can be plotted on a similar X-Y plot. A region around each enrollment point can be drawn using the information generated in the calibration set to establish a probability boundary such that a high fraction, such as 99%, of all subsequent measurements collected on each enrolled person are expected to fall within this region. For subsequent spectral biometric identification, data are collected and plotted on this same X-Y graph. If the collected data falls within one of the 99% probability regions then the person can be said to be identified as the appropriate enrolled individual. If the test data point does not lie within any of the 99% probability boundaries then the person under test is likely to not be enrolled or authorized and should retake the measurement in case there was an error in the first measurement. If the clustering of the enrolled data is such that the test data falls within two or more probability regions, then the authorization is confirmed but the identification is ambiguous. If the absolute identification is important to the task, such as for establishing personality settings in an automobile, then a probability can be calculated for each of the candidate identities and the one with greatest probability is used. Finally, if the biometric task is a verification request rather than identification, then the preceding method is followed using just the single candidate enrollment data point.

Similarly, a three-wavelength example of the application of this analysis can be envisioned, represented by clusters of data points being plotted in three-dimensional space, and the geometric distance of a target point from a cluster being determined. By extension, ten wavelengths could be selected and the distance of a target point from a cluster calculated in ten-dimensional space. While not as easily envisioned, multiple wavelengths are used in some embodiments.

In an alternative method, functions are used to preprocess spectral measurement values and the resulting function value used rather than the direct measurement. For example, measurement values taken at two wavelengths may be observed to vary up and down, opposite from one another, for an individual, but the average or total of these two values may be seen to be remain constant for that individual. In this example, a plot of the two measurements against each other from several sittings could show a cluster about a line segment having negative slope. A one-dimensional plot of the total or average would show a tight cluster about a single point. In this way, multiple wavelengths may be preprocessed with functions to result in a single value, and the single value used in place of the direct measurements. In one embodiment, functions (also known as factors, loading vectors, eigenvectors, latent variables, classification features), which represent weighted combinations of the raw measurements at each wavelength, are generated using techniques such as Principal Component Analysis, Singular Value Decomposition, Linear Discriminant Analysis, or other methods as are known to one of skill in the art. The advantages of decomposing the data into a set of factors include the increased accuracy, speed and stability of the resulting analysis, as well as a dimension reduction that may facilitate human visualization. Once the decomposition of the raw data is performed the resulting magnitudes of the factors can be used in a manner identical to the multi-wavelength examples provided above.

Selection of which wavelengths to use can affect the reliability of the identifications. One method of selecting wavelengths is discussed in U.S. Pat. No. 5,435,309, which has been incorporated by reference. In one method, wavelengths of interest are selected a priori and used for all samples. In another method, the measurements are periodically used to recalculate inter-person and intra-person differences. The addition of new otherwise closely clustered or even overlapping, individuals into an authorization database can be remedied by choosing different wavelengths, or different functions operating upon these wavelengths.

As previously, noted another factor that may affect the reliability of the identifications is the site from which tissue spectral data are taken. In use, tissue spectral data can be taken from forearm undersides of individuals, any of the phalanges on the dorsal or ventral surfaces of the fingers and thumbs, the dorsal or ventral sides of the wrist, the thenar eminence, the hypothenar eminence, the medial hypothenar eminence, or other convenient and suitable sites meeting the criteria previously described. The tissue spectral data can then be stored in a computer database accessible by, or a component of, the computational unit 37 comprised by the sampler 39. In general, either before or after storage, the magnitude of the underlying spectral shapes and properties such as factors and their magnitudes can be established. Standard outlier methodologies such as spectral F ratios, Mahalanobis distances, and Euclidean distances can be used to determine the consistency of the target spectrum with the spectral authorization database for the person with the purported identity.

In one method, after a sufficient number of calibration spectra have been collected, the calibration database is operated upon by software and discriminant analysis performed on the data, generating the appropriate factors. In one method, Principle Component Analysis is applied to the calibration data to generate factors. In another method, discriminant analysis is performed to generate factors useful in clustering the intra-person data points together, while separating the clusters at a large inter-person distance. Examples of discriminant analysis methods useful in conjunction with the present invention include linear discriminant analysis such as Fisher's discriminant analysis, and quadratic discriminant analysis, and other non-linear discriminant analysis techniques.

In one method when identity verification is desired, a tissue spectrum and purported identity are obtained from the target individual. The current tissue spectrum is subtracted from the appropriate enrollment spectrum, producing a spectral difference. The spectral difference can then be decomposed using the factors generated from the calibration dataset and the consistency between the spectral difference and the calibration set can be calculated. One calculation measures the Mahalanobis distance of the spectral difference with respect to the calibration factor set. If the distance is less than a threshold distance, then the purported identity can be positively verified. Another calculation generates the spectral residuals of the spectral difference with respect to the calibration factor set. If the residuals are less than a predetermined threshold value, then the purported identity can be positively identified. In another method, both the spectral residual and the Mahalanobis distance must be below their respective thresholds before identity is positively established.

5. Linear Spectroscopy

As previously noted, in many embodiments, both the apparatuses and the methods disclosed herein make use of the linear optical properties of the samples being measured. Non-linear optical properties (while present in minute amounts in most optical configurations) will typically become apparent at high light or energy levels due to saturation of some of the optical properties of the material being measured. Alternatively, optical nonlinearities may be observable in some materials by comparing an optical measurement (e.g. reflectance) at a given wavelength for two or more instances in which other, different wavelengths of light are also incident on the material under test. Certain materials are much more prone to displaying nonlinear optical effects.

However, the inventors have recognized, in the specific context of biometric identification, how to make productive use of the fact that optical measurements derived from skin and underlying tissue are dominated by linear effects when probed at non-harmful illumination levels. For example, some of the analyses described herein make use of the fact that the magnitude of light reflected from a piece of skin is substantially linearly related to the optical illumination power. This permits, for example, removal of the effect of a change in illumination source power by taking a mathematical ratio between the spectrum of interest and an optical reference spectrum illuminated under the same conditions, as described above. Similarly, this broad-band illumination of the source using spectroscopic systems, such as an FTIR, is substantially equivalent to the use of scanned or narrow-band illumination systems, such as those based on a wavelength-scanned spectrometer that is placed before the sample.

Thus, "linear spectroscopic analysis" is used herein to refer to an analysis that relies on the substantial linearity of the measured transmission or reflection spectrum of a sample with respect to illumination light levels. Furthermore, such an analysis may rely on the measurement of a single wavelength of the transmission or reflection spectrum being substantially unrelated to the presence or magnitude of other wavelengths of illumination light due to optical interactions of two or more wavelengths in the material being measured.

6. Experimental Tests

An experiment was conducted to test the use of the methodology disclosed herein to verify the identification of an individual. The instrumentation utilized was a near infrared Fourier transfer spectrophotometer manufactured by Perkin Elmer. The specific model used was a Perkin Elmer 2000. The sampling of the human tissue was done on the volar side of the forearm. The optical sampling device was a fiber optic sampling device that had separate fibers for launching light into the tissue and fibers for collecting the light exiting the tissue. An index matching fluid was placed between the arm and the fiber optic sampling head. The resulting intensity spectra were converted into absorbance spectra and scaled by a vector wavelength. Spectra were recorded and subsequently processed in the wavelength range of 4,200 to 7,200 cm$^{-1}$. The data consisted of sitting average spectra (5 samples per sitting) measured for 288 different people. Each were measured for a single sitting sometime within a 5-week time span. As well, there were three people measured for multiple sittings over the same 5-week span (nominally 10 times).

The framework for the investigation used a calibration model, a spectral database consisting of spectra from a large number of individuals against whom matching was performed, and a spectrum from an unknown individual (target spectrum). The verification task was to properly identify the target spectrum as either the specified person or to determine that the person did not properly identify himself.

The discrimination method applied in this case relied on Mahalanobis distance and the spectral residual magnitude that were generated when a difference spectrum was presented to the calibration model. The spectral difference was formed between the target spectrum and a test spectrum in the database. If the value of the Mahalanobis distance and the spectral residual for a given spectral difference pair were both below a prescribed level, the two spectra were determined to have come from the same individual. If one or both metrics were greater than their respective thresholds, the determination was made that the two spectra came from different individuals.

Thresholds for the two metrics were set by examining the respective cumulative distribution functions for the full-model calibration data. Two threshold values were used for this investigation: one pair that each encompassed 99% of the calibration data ("lenient") and one pair such that each encompassed only 95% of the calibration data ("stringent").

The false positive error rate was examined by using the 288 individual people's spectra in a round-robin fashion. Each was pulled out of the database and an evaluation made of how many of the remaining people in the database matched this spectrum at each of the two similarity thresholds. The false negative error rate was examined by looking at the degree of matching observed between sittings of the same person (performed for each of the three repeat people).

When the threshold values were set to the more lenient threshold (99%), the round-robin results showed the number of "matches" that occurred when each of the 288 people is pulled out from the spectral library and evaluated relative to the remaining 287 people's spectra. On average, each person matched 0.5 of another person within this database, yielding a false positive rate of 0.17%. This is the error rate that occurs when a person not in the database incorrectly specifies that he is one of the library people and the measurement confirms this.

In a subsequent test, one of the people, who was measured repeatedly over the 5 week data collection period, was compared to all other observation using the same verification methodology described above. Using the lenient threshold, every sitting matches with every other sitting, resulting in a false negative error rate of 0.0%. Results from the other two repeat people were similar.

When the verification threshold was set to the slightly more stringent standard (95%), the cross-person and same person results showed there were no matches observed across people, resulting in a false positive error rate of 0.0%. The same person, cross-sitting results show a diminished ability to match any one sitting with any other one sitting, leading to a single-sample false negative error rate of greater than 30%. However, if the spectral library consists of multiple samplings of the person in different physiologic states, the verification results can be greatly improved. In this case, if the spectral library consists of all nine of the remaining samples, then 100% of the time one or more (actually 3 or more) of the spectral library entries match the target spectrum, resulting in a false negative error rate of 0.0%. Results from the other two repeat people were similar.

Embodiments of the present invention has been disclosed with focus on in-vivo analysis on people. It is, however, recognized that the present methods and techniques can be used for in-vivo analysis of other biological organisms such as cows, horses, and other livestock to identify or confirm identity of the animal. As well, the present methods and techniques can also be applied to in-vitro analysis of blood, tissue or fluid samples to identify or confirm identity of a sample.

The biometric capabilities in the 1.1–2.5 μm NIR spectral region were also examined using a laboratory system to collect optical samples on a group of volunteer subjects. The system consisted of a 40W quartz tungsten halogen source, a fiber optic sampler assembly, a Bomem WorkIR spectrometer operating with a spectral resolution of 16 cm$^{-1}$ and a 1 mm$^2$ InGaAs detector. The optical sampler consisted of six different illumination-detection bundles that had a source-detector spacing of approximately 0.6 mm. In this case, no index matching fluid was used between the sampler and the tissue. The data were collected from 87 diabetic subjects who participated in a portion of a 17-week study. Approximately half of the subjects participated in the study for 6 weeks and half participated for 11 weeks. In either case, each person was measured during two separate visits per week for each week they participated in the study. During each measurement visit, multiple (3–5) optical samples were collected from the underside of their left forearm. Each optical sample consisted of 90 seconds of measurement time. A total of more than 5100 optical samples were collected on this study group. The resulting intensity spectra were log-transformed to pseudo-absorbance data and a scale function was applied to the spectra to make the spectral noise characteristics uniform. Standard outlier metrics (Mahalanobis Distance and Spectral F-Ratio) were applied to the resulting scaled absorbance data to remove outlying spectra before subsequent processing.

The biometric analysis was performed by randomly selecting 30 subjects' data as from authorized users ("validation"), selecting 10 that were from non-authorized users ("intruders"), and the remaining subjects' data were used to build a calibration set. The calibration data were processed to produce generic data as described in U.S. Pat. No. 6,157,041, which has been incorporated by reference. A PCA decomposition of these data was performed to generate 50 eigenvectors and scores. The scores were then analyzed to determine the 20 factors that had the largest values for the ratio of the between-person variation to the within-person variation for each set of scores.

The first two samples for each of the validation subject's data were averaged and used as 30 initial enrollment spectra. Each of the remaining validation spectra were taken in temporal sequence and subtracted from the enrollment spectrum. This spectral difference was then presented to the selected calibration factors and a Mahalanobis distance was calculated. If the Mahalanobis distance was below a certain threshold value, the validation spectrum was deemed valid, and a weighted sum of the validation spectrum (0.2) and the enrollment spectrum (0.8) was used to update the enrollment spectrum. This process was repeated for multiple threshold values. One of ordinary skill in the art will recognize that the Spectral F-Ratio could be used instead of or in conjunction with the Mahalanobis distance metric to perform the identity determinations.

Figure 4:
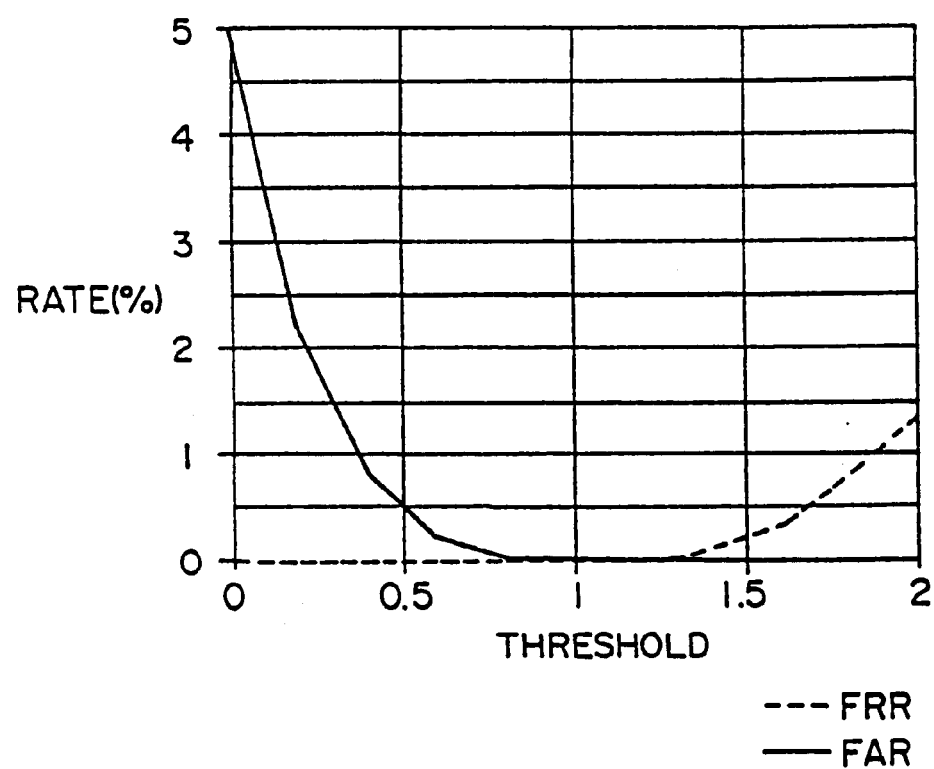
FIG. 4 is a graph depicting false acceptance rates and false rejection rates for a near-infrared biometric apparatus of the present invention.
Figure 5:
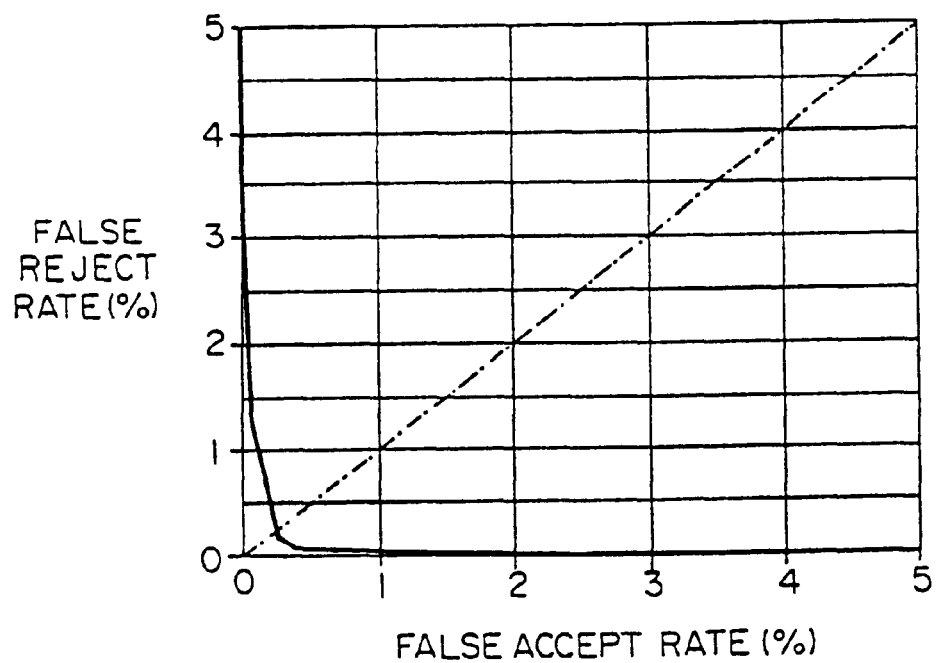
FIG. 5 is a graph summarizing receiver operating characteristics for the biometric analyzer of FIG. 4.

The intruder data was processed in a similar manner as the validation data using the same threshold values. The resulting performance plots are shown in FIGS. 4 and 5. FIG. 4 shows the false acceptance rate (FAR) and the false rejection rate (FRR) as a function of the threshold value. FIG. 5 shows the corresponding receiver operating characteristics (ROC) curve for these data. The Equal Error Rate (EER: FAR=FRR) for these data is approximately 0.2% demonstrating a high degree of biometric capability over an extended period of time.

Subsequently, the same NIR system described above was used to perform identification tasks using multiple tissue sites on numerous non-diabetic volunteers. Tissue sites that were tested and established for spectral identification and verification included the dorsal and ventral surfaces of the forearm, any of the phalanges on the dorsal or ventral surfaces of the fingers and thumbs, the dorsal or ventral sides of the wrist, the thenar eminence, the hypothenar eminence, the medial hypothenar eminence, the web between the index finger and the thumb, and the forehead. Investigation with a particular site used a methodology similar to that described above. The calibration data also included data collected at each new site used. Once the proper calibration data were collected and processed to generate factors, the site could then be used for subsequent enrollment and testing. In all cases, sites that had contralateral or multiple counterparts could be used nearly interchangeably: a person could enroll with the left index finger and use the right index finger (or any other finger) to perform the biometric task.

Figure 6:
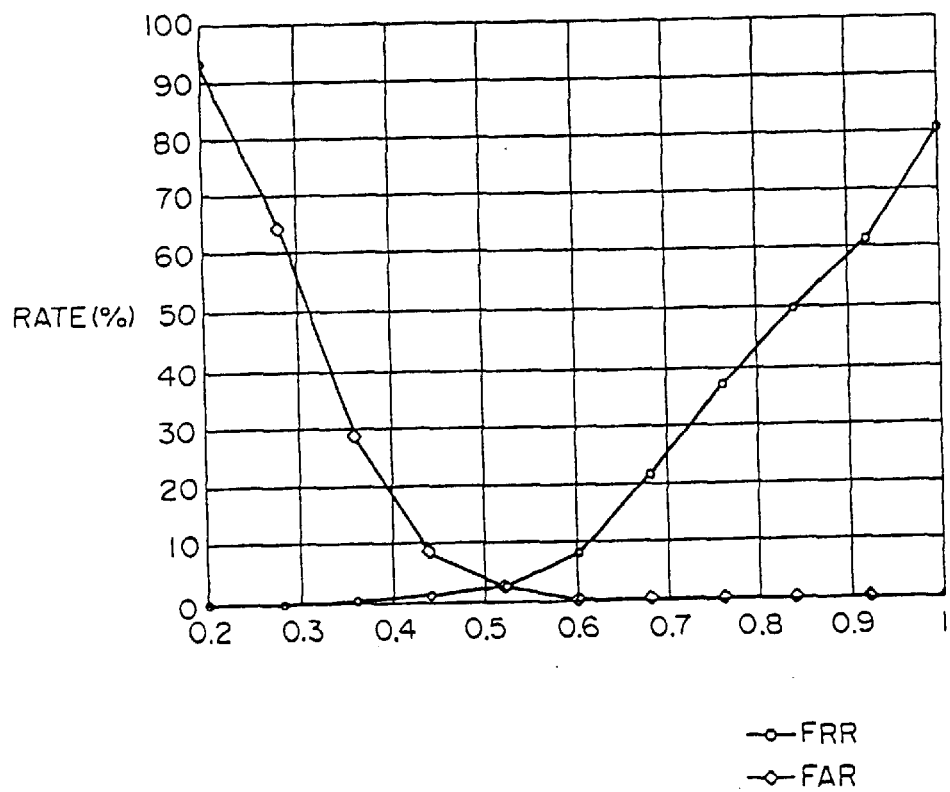
FIG. 6 is a graph depicting false acceptance rates and false rejection rates for a biometric sensor of the present invention operating in the near-ultraviolet, visible, and very near infrared region of the spectrum.
Figure 7:
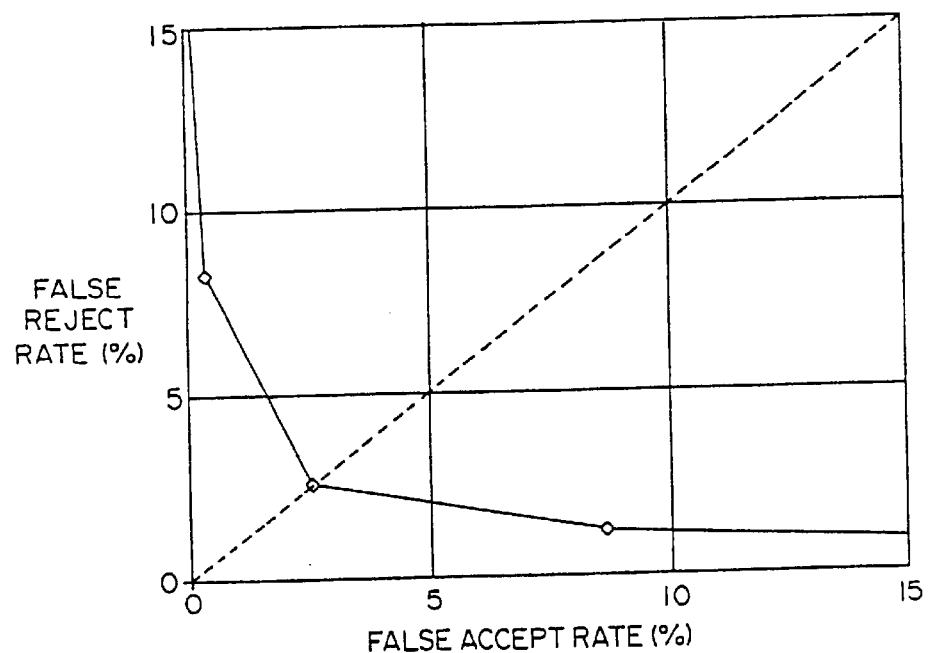
FIG. 7 is a graph depicting receiver operating conditions for the biometric sensor of FIG. 6.

The same 87 subjects that were used to collect the near infrared data described above were also simultaneously sampled with a silicon-region system. An Ocean Optics grating array spectrometer with a 1×2048 silicon linear CCD array and 12-bit digitization was used in conjunction with a fiber optical probe to collect spectral data that spanned the spectral range from 350 nm to 1000 nm. The spectral data were collapsed using an 8-point moving-window averaging filter to produce 256 data points per spectrum. These data were processed and analyzed in a manner similar to the NIR data, producing the results shown in FIG. 6 (FAR and FRR) and FIG. 7 (ROC), with an equal error rate of 2.6%. While the results are not quite as good as produced by the NIR system, they strongly indicate that biometric determinations can be made in the silicon-region. Analysis of the silicon and near infrared data showed that the silicon data contained significantly greater noise due to instrumental variation, which was likely due to a sub-optimal setup of this system and had an adverse impact on the measured results.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method for identifying an individual, the method comprising:

propagating electromagnetic radiation at the individual's skin into tissue of the individual, the electromagnetic radiation having a wavelength between 350 nm and 2.5 $\mu$m;

receiving a measured spectral variation in the form of electromagnetic radiation scattered from the tissue of the individual; and comparing the measured spectral variation with a previously stored spectral variation over a predetermined wavelength interval by comparing, at each of a plurality of wavelengths within the predetermined wavelength interval, a property of the measured and previously stored spectral variations that is independent of a presence of other wavelengths; and designating the individual as having an identity associated with the previously stored spectral variation if the measured spectral variation is consistent with the previously stored spectral variation.

2. The method recited in claim 1 wherein the property is an amplitude of the measured and previously stored spectral variations at the each of the plurality of wavelengths.

3. The method recited in claim 2 wherein comparing the measured spectral variation with the previously stored spectral variation comprises calculating a discriminant spectral variation at the each of the plurality of wavelengths from the measured and previously stored spectral variations at the each of the plurality of wavelengths.

4. The method recited in claim 3 wherein the discriminant spectral variation corresponds to a wavelength-by-wavelength difference of the measured and previously stored spectral variations.

5. The method recited in claim 3 wherein the discriminant spectral variation corresponds to a wavelength-by-wavelength ratio of the measured and previously stored spectral variations.

6. The method recited in claim 3 wherein comparing the measured spectral variation with the previously stored spectral variation further comprises determining whether the discriminant spectral variation is consistent with a calibration database of intraperson difference spectra substantially lacking in interperson spectral differences.

7. The method recited in claim 6 wherein the calibration database comprises spectral differences derived from a plurality of combinations of spectral variations over different conditions from a single individual.

8. The method recited in claim 1 wherein propagating electromagnetic radiation into tissue of the individual comprises propagating electromagnetic radiation at optical wavelengths.

9. The method recited in claim 1 wherein propagating electromagnetic radiation into tissue of the individual comprises propagating a broad spectral band.

10. The method recited in claim 1 wherein propagating electromagnetic radiation into tissue of the individual comprises propagating a plurality of signals having different wavelength characteristics.

11. The method recited in claim 1 wherein propagating electromagnetic radiation into tissue of the individual comprises propagating a time-varying sequence of wavelengths.

12. The method recited in claim 1 further comprising obtaining a purported identity of the individual, wherein the previously stored spectral variation corresponds to a spectral variation associated with the purported identity, whereby designating the individual as having the identity associated with the previously stored spectral variation corresponds to verifying the purported identity of the individual.

13. The method recited in claim 1 wherein:

the previously stored spectral variation is comprised by a plurality of previously stored spectral variations; and comparing the measured spectral variation with the previously stored spectral variation comprises comparing the measured spectral variation with each of the plurality of previously stored spectral variations.

14. A method for implementing a biometric task with respect to an individual, the method comprising:
measuring a spectral variation of electromagnetic radiation from subepidermal tissue from at least one site of the individual, the electromagnetic radiation having a wavelength between 350 nm and 2.5 µm;
performing a linear spectroscopic analysis of the spectral variation; and
performing the biometric-task in accordance with a result of the linear spectroscopic analysis.

15. The method recited in claim 14 wherein performing the biometric task comprises performing a comparison with a database to identify the individual.

16. The method recited in claim 14 wherein the at least one site comprises at least one of a dorsal and ventral surface of a proximal phalange of a finger or thumb of the individual.

17. The method recited in claim 14 wherein the at least one site comprises at least one of a dorsal and ventral surface of a medial phalange of a finger of the individual.

18. The method recited in claim 14 wherein the at least one site comprises at least one of a distal phalange of a finger or thumb of the individual.

19. The method recited in claim 14 wherein the at least one site comprises at least one of a dorsal and ventral surface of a wrist of the individual.

20. The method recited in claim 14 wherein the at least one site comprises a web between an index finger and thumb of the individual.

21. The method recited in claim 14 wherein the at least one site comprises a thenar eminence of the individual.

22. The method recited in claim 14 wherein the at least one site comprises a hypothenar eminence of the individual.

23. The method recited in claim 14 wherein the at least one site comprises a medial hypothenar eminence of the individual.

24. Apparatus for identifying an individual, the apparatus comprising:
a source of electromagnetic radiation adapted to propagate radiation at the individual's skin into tissue of the individual, the electromagnetic radiation having a wavelength between 350 nm and 2.5 µm;
a receiver adapted to receive a measured spectral variation in the form of electromagnetic radiation scattered from the tissue of the individual;
a spectral-variation database having a previously stored spectral variation; and
a computer-readable storage medium coupled with a processor, the computer-readable storage medium having a computer-readable program embodied therein for directing operation of the processor, the computer-readable program including:
instructions for comparing the measured spectral variation with the previously stored spectral variation over a predetermined wavelength interval by comparing, at each of a plurality of wavelengths within the predetermined wavelength interval, a property of the measured and previously stored spectral variations that is independent of a presence of other wavelength; and
instructions for designating the individual as having an identity associated with the previously stored spectral variation if the measured spectral variation is consistent with the previously stored spectral variation.

25. The apparatus recited in claim 24 wherein the property is an amplitude of the measured and previously stored spectral variations at the each of the plurality of wavelengths.

26. The apparatus recited in claim 25 wherein the instructions for comparing the measured spectral variation with the previously stored spectral variation comprise instructions for calculating a discriminant spectral variation at the each of the plurality of wavelengths from the measured and previously stored spectral variations at the each of the plurality of wavelengths.

27. The apparatus recited in claim 26 wherein the discriminant spectral variation corresponds to a wavelength-by-wavelength different of the measured and previously stored spectral variations.

28. The apparatus recited in claim 26 wherein the discriminant spectral variation corresponds to a wavelength-by-wavelength ratio of the measured and previously stored spectral variations.

29. The apparatus recited in claim 26 further comprising a calibration database having a plurality of intraperson difference spectra, wherein the instructions for comparing the measured spectral variation with the previously stored spectral variation further comprise instructions for determining whether the discriminant spectral variation is consistent with the calibration database.

30. The apparatus recited in claim 29 wherein the calibration database comprises spectral differences derived from a plurality of combinations of spectral variations over different conditions from a single individual.

31. The apparatus recited in claim 24 wherein the source of electromagnetic radiation comprises a source of radiation at optical wavelengths.

32. The apparatus recited in claim 24 wherein the source of electromagnetic radiation comprises a broad-spectral-band source.

33. The apparatus recited in claim 24 wherein the source of electromagnetic radiation comprises a plurality of sources having different wavelength characteristics.

34. The apparatus recited in claim 24 wherein the source of electromagnetic radiation is adapted to propagate a time-varying sequence of wavelengths.

35. The apparatus recited in claim 24 wherein:
the spectral-variation database comprises a plurality of previously stored spectral variations; and
the instructions for comparing the measured spectral variation with the previously stored spectral variation comprises instructions for comparing the measured spectral variation with each of the plurality of previously stored spectral variations.

36. Apparatus for identifying an individual, the apparatus comprising:
means for propagating electromagnetic radiation at the individual's skin into tissue of the individual, the electromagnetic radiation having a wavelength between 350 nm and 2.5 µm;
means for receiving a measured spectral variation in the form of electromagnetic radiation scattered from the tissue of the individual;
means for comparing the measured spectral variation with a previously stored spectral variation over a predetermined wavelength interval by comparing, at each of a plurality of wavelength within the predetermined wavelength interval, a property of the measured and previously stored spectral variations that is independent of a presence of other wavelengths; and means for designating the individual as having an identity associated with the previously stored spectral variation if the measured spectral variation is consistent with the previously stored spectral variation.

37. The apparatus recited in claim 36 wherein the property is an amplitude of the measured and previously stored spectral variations at each of the plurality of wavelengths.

38. The apparatus recited in claim 36 wherein the means for propagating electromagnetic radiation into tissue of the individual comprises means for propagating electromagnetic radiation at optical wavelengths.

39. The apparatus recited in claim 36 wherein the means for propagating electromagnetic radiation into tissue of the individual comprises means for propagating a broad spectral band.

40. The apparatus recited in claim 36 wherein the means for propagating electromagnetic radiation into tissue of the individual comprises a plurality of means for propagating signals having different wavelength characteristics.

* * * * *